(12) United States Patent
Voelcker et al.

(10) Patent No.: US 10,234,390 B2
(45) Date of Patent: Mar. 19, 2019

(54) OPTICAL BIOSENSOR

(71) Applicant: Nicolas H. Voelcker, Blackwood (AU)

(72) Inventors: Nicolas H. Voelcker, Blackwood (AU); Fransiska Sri Herwahyu Krismastuti, Mawson Lakes (AU); Beatriz Prieto Simon, Adelaide (AU)

(73) Assignee: Nicholas H. Voelcker, Blackwood (AU)

( * ) Notice: Subject to any disclaimer, the term of this patent is extended or adjusted under 35 U.S.C. 154(b) by 32 days.

(21) Appl. No.: 15/318,065

(22) PCT Filed: Mar. 3, 2015

(86) PCT No.: PCT/AU2015/000118
§ 371 (c)(1),
(2) Date: Dec. 12, 2016

(87) PCT Pub. No.: WO2015/188215
PCT Pub. Date: Dec. 17, 2015

(65) Prior Publication Data
US 2017/0108437 A1    Apr. 20, 2017

(30) Foreign Application Priority Data
Jun. 12, 2014 (AU) .............................. 2014902236

(51) Int. Cl.
*G01N 33/552* (2006.01)
*G01N 33/553* (2006.01)
(Continued)

(52) U.S. Cl.
CPC ....... *G01N 21/6428* (2013.01); *G01N 33/552* (2013.01); *G01N 33/553* (2013.01);
(Continued)

(58) Field of Classification Search
None
See application file for complete search history.

(56) References Cited

U.S. PATENT DOCUMENTS

2005/0147534 A1   7/2005  Swager et al.
2005/0191643 A1   9/2005  Haugland et al.
(Continued)

OTHER PUBLICATIONS

Palestino et al.; "Biosensing and Protein Fluorescence Enhancement by Functionalized Porous Silicon Devices"; Langmuir; 2008; pp. 13765-13771; vol. 24; American Chemical Society.
(Continued)

*Primary Examiner* — Christopher L Chin
(74) *Attorney, Agent, or Firm* — The Webb Law Firm

(57) ABSTRACT

Provided herein is an optical biosensor for detecting a target bioanalyte in a sample. The biosensor includes: a porous silicon or alumina substrate having a surface and a detection agent immobilised on the surface. The detection agent includes a sensing domain and a signaling domain, the sensing domain having a linker capable of interacting with the target bioanalyte and the signaling domain having a luminescence donor and a luminescence acceptor wherein the luminescence donor and the luminescence acceptor are connected by the linker and are optically coupled in the absence of the target bioanalyte. Emission of light from the luminescence donor is substantially quenched by the luminescence acceptor, and interaction of the target bioanalyte with the linker results in optical un-coupling of the luminescence donor and the luminescence acceptor to thereby result in light emission from the luminescence donor.

19 Claims, 16 Drawing Sheets
Specification includes a Sequence Listing.

(51) Int. Cl.
   *G01N 21/64* (2006.01)
   *G01N 33/573* (2006.01)
   *G01N 33/551* (2006.01)

(52) U.S. Cl.
   CPC ......... *G01N 33/573* (2013.01); *G01N 33/551* (2013.01); *G01N 2021/6432* (2013.01); *G01N 2201/068* (2013.01); *G01N 2333/95* (2013.01)

(56) References Cited

U.S. PATENT DOCUMENTS

| | | |
|---|---|---|
| 2009/0081662 A1 | 3/2009 | Soukka et al. |
| 2014/0045761 A1 | 2/2014 | Gibson |

OTHER PUBLICATIONS

Palestino et al.; "Optical Characterization of Porous Silicon Microcavities for Glucose Oxidase Biosensing."; Proc. of SPIE; 2008; pp. 69911Y-1-69911Y-10; vol. 6991.

Parthasarathy et al.; "Sortase A as a Novel Molecular "Stapler" for Sequence-Specific Protein Conjugation"; Bioconjugate Chem.; 2007; pp. 469-476; vol. 18; American Chemical Society.

Rundhaug; "Matrix Metalloproteinases, Angiogenesis, and Cancer"; Clinical Cancer Research; 2003; pp. 551-554; vol. 9.

Saarialho-Kere; "Patterns of matrix metalloproteinase and TIMP expression in chronic ulcers"; Arch. Dermatol. Res.; 1998; pp. S47-S54; vol. 290 (Suppl.); Springer-Verlag.

Sam et al.; "Semiquantitative Study of the EDC/NHS Activation of Acid Terminal Groups at Modified Porous Silicon Surfaces"; Langmuir; 2010; pp. 809-814; vol. 26:2; American Chemical Society.

Sciacca et al.; "Doubly resonant porous silicon microcavities for enhanced detection of fluorescent organic molecules"; Sensors and Actuators B: Chemical; 2009; pp. 467-470; vol. 137; Elsevier B.V.

Sciacca et al.; "Chitosan-functionalized porous silicon optical transducer for the detection of carboxylic acid-containing drugs in water"; J. Mater. Chem.; 2010; 9 pgs.; The Royal Society of Chemistry.

Sen et al.; "Human skin wounds: A major and snowballing threat to public health and the economy"; Wound Rep. Reg.; 2009; pp. 763-771; vol. 17; The Wound Healing Society.

Tarnuzzer et al.; "Biochemical analysis of acute and chronic wound environments"; Wound Rep. Reg.; 1996; pp. 321-325; vol. 4; The Wound Healing Society.

Thet et al.; "Visible, colorimetric dissemination between pathogenic strains of *Staphylococcus aureus* and *Pseudomonas aeruginosa* using fluorescent dye containing lipid vesicles"; Biosensors and Bioelectronics; 2013; pp. 538-543; vol. 41; Elsevier B.V.

Trengove et al.; "Analysis of the acute and chronic wound environments: the role of proteases and their inhibitors"; Wound Rep. Reg.; 1999; pp. 442-452; vol. 7; The Wound Healing Society.

Velnar et al.; "The Wound Healing Process: an Overview of the Cellular and Molecular Mechanisms"; The Journal of International Medical Research; 2009; pp. 1528-1542; vol. 37.

Venturello et al.; "Controlled light emission from dye-impregnated porous silicon microcavities"; Journal of Non-Crystalline Solids; 2006; pp. 1230-1233; vol. 352; Elsevier B.V.

Verma et al.; "Matrix metalloproteinases (MMPs): Chemical-biological functions and (Q)SARs"; Bioorganic & Medicinal Chemistry; 2007; pp. 2223-2268; vol. 15; Elsevier Ltd.

Visse et al.; "Matrix Metalloproteinases and Tissue Inhibitors of Metalloproteinases: Structure, Function, and Biochemistry"; Circ. Res.; 2003; 21 pgs.; vol. 92; American Heart Association.

Woessner, Jr.; "Matrix metalloproteinases and their inhibitors in connective tissue remodeling"; The FASEB Journal; 1991; pp. 2145-2154; vol. 5; FASEB.

World Union of Wound Healing Societies (WUWHS); "Principles of best practice: Diagnostics and wounds. A consensus document."; 2008; pp. 1-10; Medical Education Partnership (MEP) Ltd.; London, England.

Yager et al.; "The proteolytic environment of chronic wounds"; Wound Rep. Reg.; 1999; pp. 433-441; vol. 7; The Wound Healing Society.

Zhou et al.; "A Thin Film Detection/Response System for Pathogenic Bacteria"; J. Am. Chem. Soc.; 2010; pp. 6566-6570; vol. 132; American Chemical Society.

Zhou et al.; "Development of a prototype wound dressing technology which can detect and report colonization by pathogenic bacteria"; Biosensors and Bioelectronics; 2011; 10 pgs.; vol. 30:1.

Anglin et al.; "Porous silicon in drug delivery devices and materials"; Advanced Drug Delivery Reviews; 2008, pp. 1266-1277; vol. 60; Elsevier B.V.

Arroyo-Hernandez et al.; "Biofunctionalization of surfaces of nanostructured porous silicon"; Materials Science and Engineering; 2003; pp. 697-701; vol. C23; Elsevier B.V.

Beekman et al.; "Convenient fluorometric assay for matrix metalloproteinase activity and its application in biological media"; FEBS Letters; 1996; pp. 221-225; vol. 390; Federation of European Biochemical Societies.

Bigg et al.; "The inhibition of metalloproteinases as a therapeutic target in rheumatoid arthritis and osteoarthritis"; Current Opinion in Pharmacology; 2001; pp. 314-320; vol. 1, Elsevier Science Ltd.

Bocking et al.; "Immobilization of dendrimers on Si-C linked carboxylic acid-terminated monolayers on silicon(111)"; Thin Solid Films; 2006; pp. 1857-1863; vol. 515; Elsevier B.V.

Bocking et al.; "Modifying Porous Silicon with Self-Assembled Monolayers for Biomedical Applications: The Influence of Surface Coverage on Stability and Biomolecule Coupling"; Adv. Funct. Mater.; 2008; pp. 3827-3833; vol. 18; Wiley-VCH Verlag GmbH & Co. KGaA; Weinheim, Germany.

Bode et al.; "Structural properties of matrix metalloproteinases"; Cell. Mol. Life Sci.; 1999; pp. 639-652; vol. 55; Birkhauser Verlag; Basel, Switzerland.

Born et al.; "Principles of optics: Electromagnetic theory of propagation, interference and diffraction of light"; Seventh (expanded) edition; 2003; pp. xvi-20; Cambridge University Press; Cambridge, United Kingdom.

Boukherroub et al.; "Passivated Luminescent Porous Silicon"; Journal of the Electrochemical Society; 2001; pp. H91-H97; vol. 148:9; The Electrochemical Society, Inc.

Boukherroub et al.; "Thermal Hydrosilylation of Undecylenic Acid with Porous Silicon"; Journal of the Electrochemical Society; 2002; pp. H59-H63; vol. 149:2; The Electrochemical Society, Inc.

Brem et al.; "Molecular Markers in Patients with Chronic Wounds to Guide Surgical Debridement"; Mol. Med.; 2007; pp. 30-39; vol. 13:1-2.

Cao et al.; "A peptidomimetic inhibitor of matrix metalloproteinases containing a tetherable linker group"; 2010; pp. 1-30; QUT Digital Repository.

Chan et al.; "Identification of Gram Negative Bacteria Using Nanoscale Silicon Microcavities"; J. Am. Chem. Soc.; 2001; pp. 11797-11798; vol. 123; American Chemical Society.

Chan et al.; "Nanoscale silicon microcavities for biosensing"; Materials Science and Engineering; 2001; pp. 277-282; vol. C15; Elsevier Science B.V.

Clapp et al.; "Fluorescence Resonance Energy Transfer Between Quantum Dot Donors and Dye-Labeled Protein Acceptors"; J. Am. Chem. Soc.; 2004; pp. 301-310; vol. 126; American Chemical Society.

Dargaville et al.; "Sensors and imaging for wound healing: a review"; Biosensors and Bioelectronics; 2013; 37 pgs.; vol. 41; Elsevier B.V.

Delouise et al.; "Cross-Correlation of Optical Microcavity Biosensor Response with Immobilized Enzyme Activity. Insights into Biosensor Sensitivity"; Analytical Chemistry; 2005; pp. 3222-3230; vol. 77; American Chemical Society.

Delouise et al.; "Hydrogel-Supported Optical-Microcavity Sensors"; Adv. Mater.; 2005; pp. 2199-2203; vol. 17; Wiley-VCH Verlag GmbH & Co. KGaA; Weinheim, Germany.

De Stefano et al.; "Smart optical sensors for chemical substances based on porous silicon technology"; Applied Optics; 2004; pp. 167-172; vol. 43:1; Optical Society of America.

(56) References Cited

OTHER PUBLICATIONS

De Stefano et al.; "Hybrid polymer-porous silicon photonic crystals for optical sensing"; J. Appl. Phys.; 2009; pp. 023109-1-023109-5; vol. 106; American Institute of Physics.
Do et al.; "A microcavity based on a porous silicon multilayer"; Adv. Nat. Sci.: Nanosci. Nanotechnol.; 2011; pp. 1-5; vol. 2; Vietnam Academy of Science & Technology.
Eming et al.; "Differential Proteomic Analysis Distinguishes Tissue Repair Biomarker Signatures in Wound Exudates Obtained from Normal Healing and Chronic Wounds"; Journal of Proteome Research; 2010; pp. 4758-4766; vol. 9; American Chemical Society.
Gao et al.; "Label-Free Colorimetric Detection of Gelatinases on Nanoporous Silicon Photonic Films"; Analytical Chemistry; 2008; pp. 1468-1473; vol. 80:5; American Chemical Society.
Gogly et al.; "Collagen Zymography as a Sensitive and Specific Technique for the Determination of Subpicogram Levels of Interstitial Collagenase"; Analytical Biochemistry; 1998; pp. 211-216; vol. 255; Academic Press.
Gorman et al.; "Regulation of matrix metalloproteinase expression"; Drug Discov Today: Dis Model; 2011; 7 pages; Elsevier Ltd.
Guan et al.; "Mesoporous silicon photonic crystal microparticles: towards single-cell optical biosensors"; Faraday Discuss.; 2011; pp. 301-317; vol. 149; The Royal Society of Chemistry.
Hanson et al.; "Understanding Wound Fluid and the Phases of Healing"; Advances in Skin & Wound Care; 2005; pp. 360-362; vol. 18:7; Lippincott Williams & Wilkins.
Harding et al.; "Healing chronic wounds"; BMJ; 2002; pp. 160-163; vol. 324.
Hurley et al.; "Nanopatterning of Alkynes on Hydrogen-Terminated Silicon Surfaces by Scanning Probe-Induced Cathodic Electrografting"; J. Am. Chem. Soc.; 2003; pp. 11334-11339; vol. 125; American Chemical Society.
Iyer et al.; "Crystal Structure of an Active Form of Human MMP-1"; J. Mol. Biol.; 2006; pp. 78-88; vol. 362; Elsevier Ltd.
Jane et al.; "Porous silicon biosensors on the advance"; Trends in Biotechnology; 2009; pp. 230-239; vol. 27:4; Cell Press.
Jung et al.; "Rapid analysis of matrix metalloproteinase-3 activity by gelatin arrays using a spectral surface plasmon resonance biosensor"; Analyst; 2010; pp. 1050-1057; vol. 135; The Royal Society of Chemistry.
Kilian et al.; "Smart Tissue Culture: in Situ Monitoring of the Activity of Protease Enzymes Secreted from Live Cells Using Nanostructured Photonic Crystals"; Nano Letters; 2009; pp. 2021-2025; vol. 9:5; American Chemical Society.
Kilian et al.; "The importance of surface chemistry in mesoporous materials: lessons from porous silicon biosensors"; Chem. Commun.; 2009; pp. 630-640; The Royal Society of Chemistry.
Krismastuti et al.; "Matrix Metalloproteinase Biosensor Based on a Porous Silicon Reflector"; Aust. J. Chem.; 2013; pp. 1428-1434; vol. 66; CSIRO Publishing.
Lakowicz; "Principles of Fluorescence Spectroscopy", Third Edition; 2006; pp. vii-26; Springer; Singapore.
Li et al.; "A porous silicon optical microcavity for sensitive bacteria detection"; Nanotechnology; 2011; pp. 1-6; vol. 22; IOP Publishing Ltd.
Lin et al.; "A Porous Silicon-Based Optical Interferometric Biosensor"; Science; 1997; pp. 840-843; vol. 278; ProQuest.
Lombard et al.; "Assays of Matrix Metalloproteinases (MMPs) activities: a review"; Biochimie; 2005; pp. 265-272; vol. 87; Elsevier SAS.
Low et al; "The biocompatibility of porous silicon in tissues of the eye"; Biomaterials; 2009; pp. 2873-2880; vol. 30; Elsevier Ltd.
Martin et al.; "Matrix metalloproteinase sensing via porous silicon microcavity devices functionalized with human antibodies"; Phys. Status Solidi. C; 2011, pp. 1888-1892; vol. 8:6; Wiley-VCH Verlag GmbH & Co. KGaA; Weinheim, Germany.
Mast et al.; "Interactions of cytokines, growth factors, and proteases in acute and chronic wounds"; Wound Rep. Reg.; 1996; pp. 411-420; vol. 4; The Wound Healing Society.
Mehmood et al.; "Applications of modern sensors and wireless technology in effective wound management"; J. Biomed. Mater. Res. Part B; 2013; pp. 1-11; Wiley Periodicals, Inc.
Munge et al.; "Sensitive electrochemical immunosensor for matrix metalloproteinase-3 based on single-wall carbon nanotubes"; Analyst; 2010; pp. 1345-1350; vol. 135; The Royal Society of Chemistry.
Ouyang et al.; "Biosensing using Porous Silicon Photonic Bandgap Structures"; SPIE Optics East; 2005; 15 pgs.; Department of Electrical and Computer Engineering, University of Rochester; Rochester, New York.
Ouyang et al.; "Label-Free Quantitative Detection of Protein Using Macroporous Silicon Photonic Bandgap Biosensors"; Anal. Chem.; 2007; pp. 1502-1506; vol. 79:4; American Chemical Society.
Ouyang et al.; "Macroporous Silicon Microcavities for Macromolecule Detection"; Adv. Funct. Mater.; 2005; pp. 1851-1859; vol. 15; Wiley-VCH Verlag GmbH & Co. KGaA; Weinheim, Germany.
Ouyang et al.; "Quantitative analysis of the sensitivity of porous silicon optical biosensors"; Appl. Phys. Lett.; 2006; pp. 163108-1-163108-3; vol. 88; American Institute of Physics.
Pace et al.; "Study of the optical properties of a thermoresponsive polymer grafted onto porous silicon scaffolds"; New J. Chem.; 2013; pp. 228-235; vol. 37; The Royal Society of Chemistry and the Centre National de la Recherche Scientifique.
Pacholski et al.; "Biosensing Using Porous Silicon Double-Layer Interferometers: Reflective Interferometric Fourier Transform Spectroscopy"; J. Am. Chem. Soc.; 2005; pp. 1-25; vol. 127:33.
Krismastuti et al.; "Porous Silicon Resonant Microcavity Biosensor for Matrix Metalloproteinase Detection"; Adv. Funct. Mater; 2014; pp. 3639-3650; vol. 24.

OPTICAL BIOSENSOR

CROSS-REFERENCE TO RELATED APPLICATIONS

This application is the United States national phase of International Application No. PCT/AU205/000118 filed Mar. 3, 2015, and claims priority to Australian Patent Application No. 2014902236 filed Jun. 12, 2014, the disclosures of which are hereby incorporated in their entirety by reference.

The Sequence Listing associated with this application is filed in electronic format via EFS-Web and is hereby incorporated by reference into the specification in its entirety. The name of the text file containing the Sequence Listing is 1606170_ST25.txt. The size of the text file is 992 bytes, and the text file was created on Dec. 8, 2016.

PRIORITY DOCUMENTS

The present application claims priority from Australian Provisional Patent Application No. 2014902236 titled "OPTICAL BIOSENSOR" and filed on 12 Jun. 2014, the content of which is hereby incorporated by reference in its entirety.

FIELD

The present invention relates to optical biosensors for the detection of bioanalytes, such as peptides and proteins. In a particular form, the present invention relates to optical biosensors for the detection of peptides and proteins that are associated with specific diseases or pathological conditions.

BACKGROUND

Detection of peptides, proteins and other biological analytes ("bioanalytes") that are associated with a particular disease or pathological condition permits the diagnosis and prognosis of the disease or condition. For example, several cardiac marker proteins, such as acute coronary syndromes (ACS) and C-reactive protein (CRP), have been identified and are used for the diagnosis and prognosis of cardiovascular diseases.

Diagnostic tools used for detecting or quantifying bioanalytes typically rely on ligand-specific binding between a ligand and a receptor. Ligand/receptor binding pairs used commonly in diagnostics include antigen-antibody, hormone-receptor, drug-receptor, cell surface antigen-lectin, biotin-avidin, substrate/enzyme, and complementary nucleic acid strands. The bioanalyte to be detected may be either member of the binding pair; alternatively, the bioanalyte may be a ligand analogue that competes with the ligand for binding to the complement receptor.

A range of devices for detecting ligand/receptor interactions are known. For example, chemical/enzymatic assays are used in which the presence or amount of bioanalyte is detected by measuring or quantifying a detectable reaction product, such as gold immunoparticles. Ligand/receptor interactions can also be detected and quantified by radiolabel assays. Specifically, a frequently used assay method is enzyme linked immunosorbent assay (ELISA). Although very accurate, it is time-consuming, expensive, and technically complicated.

Biosensors that detect bioanalytes associated with wounds would be beneficial in the management of chronic wounds such as diabetic foot ulcers, pressure ulcers and venous leg ulcers. Management of these wounds is lengthy and challenging due to the inherent complexity of the biochemical processes occurring in non-healing wounds. Typically, regular examinations and assessments of the wound bed are performed by nurses and clinicians to inform the individual subject's wound treatment plan. This assessment process consumes a significant amount of nursing time and dressing materials, which contribute to increasing medical costs in wound care.

The use of advanced detection technologies, such as diagnostic and theranostic biosensors in wound management, especially for monitoring the healing status of acute and chronic wounds, is rapidly growing.[2, 6] The ideal diagnostic tool would afford a clear and simple read-out, not requiring interpretation from a medical expert, while a theranostic would release therapeutics in response to altered wound healing,[1, 2, 6] for instance as a result of bacterial infection.[7-9] It would be desirable for such diagnostic or theranostic biosensors to be incorporated into a wound dressing (a 'smart' dressing) or deployed as a point-of-care (POC) device that is fast, responsive and is both sensitive and selective.

There is a need for diagnostic tools that provide fast, sensitive, selective and/or low-cost detection of biomarkers of wound status or other diseases or pathological conditions.

SUMMARY

According to a first aspect, there is provided an optical biosensor for detecting a target bioanalyte in a sample, the biosensor comprising:
  a porous silicon or alumina substrate comprising a surface and a detection agent immobilised on the surface, the detection agent comprising a sensing domain and a signaling domain, the sensing domain comprising a linker capable of interacting with the target bioanalyte and the signaling domain comprising a luminescence donor and a luminescence acceptor wherein the luminescence donor and the luminescence acceptor are connected by the linker and are optically coupled in the absence of the target bioanalyte such that emission of light from the luminescence donor is substantially quenched by the luminescence acceptor, and interaction of the target bioanalyte with the linker results in optical un-coupling of the luminescence donor and the luminescence acceptor to thereby result in light emission from the luminescence donor, and
  a plurality of light interacting pores on the surface of the substrate, wherein the pores are configured to interact with the light emission from the luminescence donor to provide a measurable light emission which is indicative of the presence of the target bioanalyte.

In certain embodiments, an internal surface of the light interacting pores comprises an optical structure that interacts with the light emission from the luminescence donor. The optical structure may be an optical filter, reflector or cavity. For example, the internal surface of the light interacting pores may comprise a Bragg reflector, a rugate filter, a resonant microcavity, or a combination of any of these optical features. In certain embodiments, the substrate is a resonant microcavity (pSiRM) substrate in which the light interacting pores comprise distributed Bragg reflectors separated by a resonant microcavity.

The luminescence donor and the luminescence acceptor may be a fluorescence donor/acceptor pair or a phosphorescence donor/acceptor pair.

The optical biosensor may further comprise a detector for detecting light emission from the luminescence donor and provide an output signal containing information on said light emission.

Advantageously, the measurable light emission is enhanced or amplified relative to the light emission that would be measured in the absence of the light interacting pores on the surface of the substrate. This means that higher levels of detection can be obtained using the biosensor described herein relative to a biosensor that does not include the light interacting pores.

In certain embodiments, the biosensor further comprises a bioanalyte specific capture agent. The bioanalyte specific capture agent may comprise a binding agent capable of selectively binding the target bioanalyte. The bioanalyte specific capture agent may be deposited on or near the surface of the porous silicon or alumina substrate so that at least some of any bioanalyte captured by the capture agent is capable of interacting with the sensing domain of the detection agent. The bioanalyte specific capture agent may be in the form of particles comprising binding agent on the surface thereof. For example, the particles may be functionalised magnetic nanoparticles (MNPs) having binding agent bound to a surface thereof. The functionalised MNPs may interact with and be retained on the surface of the substrate.

The binding agent may be any agent that selectively binds the target bioanalyte. The binding agent may bind the target bioanalyte selectively from complex fluids comprising other components that are structurally related to the target bioanalyte. For example, the biosensor of these embodiments may be used for the selective detection of a specific peptide or protein in a family of structurally related peptides or proteins.

According to a second aspect, there is provided a method for detecting a target bioanalyte in a sample, the method comprising:
  providing an optical biosensor comprising: a porous silicon or alumina substrate comprising a surface and a detection agent immobilised on the surface, the detection agent comprising a sensing domain and a signaling domain, the sensing domain comprising a linker capable of interacting with the target bioanalyte and the signaling domain comprising a luminescence donor and a luminescence acceptor wherein the luminescence donor and the luminescence acceptor are connected by the linker and are optically coupled in the absence of the target bioanalyte such that emission of light from the luminescence donor is substantially quenched by the luminescence acceptor, and interaction of the target bioanalyte with the linker results in optical un-coupling of the luminescence donor and the luminescence acceptor to thereby result in light emission from the luminescence donor, and a plurality of light interacting pores on the surface of the substrate, wherein the pores are configured to interact with the light emission from the luminescence donor to provide a measurable light emission which is indicative of the presence of the target bioanalyte;
  contacting the surface of the optical biosensor with the sample to allow interaction of the target bioanalyte (if present) and the linker; and
  detecting a change in light emission from the optical biosensor.

According to a third aspect, there is provided a method for measuring the concentration of a target bioanalyte in a sample, the method comprising:
  providing an optical biosensor comprising: a porous silicon or alumina substrate comprising a surface and a detection agent immobilised on the surface, the detection agent comprising a sensing domain and a signaling domain, the sensing domain comprising a linker capable of interacting with the target bioanalyte and the signaling domain comprising a luminescence donor and a luminescence acceptor wherein the luminescence donor and the luminescence acceptor are connected by the linker and are optically coupled in the absence of the target bioanalyte such that emission of light from the luminescence donor is substantially quenched by the luminescence acceptor, and interaction of the target bioanalyte with the linker results in optical un-coupling of the luminescence donor and the luminescence acceptor to thereby result in light emission from the luminescence donor, and a plurality of light interacting pores on the surface of the substrate, wherein the pores are configured to interact with the light emission from the luminescence donor to provide a measurable light emission which is indicative of the presence of the target bioanalyte;
  contacting the surface of the optical biosensor with the sample to allow interaction of the target bioanalyte (if present) and the linker;
  detecting a change in light emission from the optical biosensor, and
  determining the concentration of the target bioanalyte in the sample from the change in the light emission.

In certain embodiments of the second and third aspects, the change in light emission may be any one of a change in the wavelength of the light emitted and/or a change in the intensity of the light emitted from the optical biosensor.

In certain embodiments of the first, second and third aspects, the linker is cleavable by the target bioanalyte when it contacts the linker such that cleavage of the linker results in optical un-coupling of the luminescence donor and the luminescence acceptor.

In certain embodiments of the first, second and third aspects, the light interacting pores comprise a resonant microcavity and the substrate shows a resonance microcavity dip in the centre of the reflectance band in a reflectance spectrum and the wavelength of the microcavity dip is substantially the same as the emission wavelength of the luminescence donor so that the emission from the luminescence donor is enhanced by the microcavity. In these embodiments, the resonance microcavity dip of the pSiRM is sensitive to refractive index changes and a relatively small refractive index change induces a relatively large shift in the optical spectrum. In these embodiments, the shift in the optical spectrum is also indicative of the presence of the target bioanalyte.

The microcavity may be formed in porous silicon or porous alumina. In certain embodiments, the microcavity is formed in porous silicon.

In certain embodiments, the light interacting pores comprise a distributed Bragg reflector with each reflector comprising a periodic layer structure alternating between high porosity silicon and low porosity silicon.

In certain embodiments, the substrate is a resonant microcavity (pSiRM) substrate in which the light interacting pores comprise distributed Bragg reflectors separated by a resonant microcavity. The optical thickness of each distributed Bragg reflector is a quarter-wavelength and the optical thickness of the microcavity is a multiple of a half-wavelength and the wavelength is the emission wavelength of the fluorescence donor.

In certain embodiments of the first, second and third aspects, the target bioanalyte is a peptide or protein of interest. In specific embodiments, the target bioanalyte is an enzyme.

In certain embodiments, the biosensor further comprises a bioanalyte specific capture agent. The bioanalyte specific capture agent may comprise a binding agent capable of selectively binding the target bioanalyte. The bioanalyte specific capture agent may be deposited on or near the surface of the porous silicon or alumina substrate so that at least some of any bioanalyte captured by the capture agent is capable of interacting with the sensing domain of the detection agent. The bioanalyte specific capture agent may be in the form of particles comprising binding agent on the surface thereof. For example, the particles may be functionalised magnetic nanoparticles (MNPs) having binding agent bound to a surface thereof. The functionalised MNPs may interact with and be retained on the surface of the substrate.

The binding agent may be any agent that selectively binds the target bioanalyte. The binding agent may bind the target bioanalyte selectively from complex fluids comprising other components that are structurally related to the target bioanalyte. For example, the biosensor of these embodiments may be used for the selective detection of a specific peptide or protein in a family of structurally related peptides or proteins.

In certain embodiments, the target bioanalyte is a matrix metalloproteinase (MMP). MMPs are clinically validated biomarkers in chronic wounds. Accordingly, in a fourth aspect there is provided a method for monitoring and/or assessing wound status in a subject, the method comprising:

providing an optical biosensor for detecting a matrix metalloproteinase in a wound fluid from said subject, the biosensor comprising: a porous silicon or alumina substrate comprising a surface and a detection agent immobilised on the surface, the detection agent comprising a sensing domain and a signaling domain, the sensing domain comprising a linker that is a substrate for the matrix metalloproteinase and the signaling domain comprising a luminescence donor and a luminescence acceptor wherein the luminescence donor and the luminescence acceptor are connected by the linker and are optically coupled such that emission of light from the luminescence donor is substantially quenched by the luminescence acceptor, and interaction of the matrix metalloproteinase with the linker results in cleavage of the linker and optical un-coupling of the luminescence donor and the luminescence acceptor to thereby result in light emission from the luminescence donor, and a plurality of light interacting pores on the surface of the substrate, wherein the pores are configured to interact with the light emission from the luminescence donor to provide a measurable light emission which is indicative of the presence of the matrix metalloproteinase;

contacting the surface of the optical biosensor with a sample of the wound fluid to allow interaction of the matrix metalloproteinase (if present) and the linker, detecting a change in light emission from the optical biosensor, and using the detected change in light emission to provide an indication of wound status.

MMPs have also been strongly implicated in multiple stages of cancer progression including the acquisition of invasive and metastatic properties.[71] Accordingly, in a fifth aspect there is provided a method for monitoring and/or assessing cancer status in a subject, the method comprising:

providing an optical biosensor for detecting a matrix metalloproteinase in cancer tissue or blood from said subject, the biosensor comprising: a porous silicon or alumina substrate comprising a surface and a detection agent immobilised on the surface, the detection agent comprising a sensing domain and a signaling domain, the sensing domain comprising a linker that is a substrate for the matrix metalloproteinase and the signaling domain comprising a luminescence donor and a luminescence acceptor wherein the luminescence donor and the luminescence acceptor are connected by the linker and are optically coupled such that emission of light from the luminescence donor is substantially quenched by the luminescence acceptor, and interaction of the matrix metalloproteinase with the linker results in cleavage of the linker and optical un-coupling of the luminescence donor and the luminescence acceptor to thereby result in light emission from the luminescence donor, and a plurality of light interacting pores on the surface of the substrate, wherein the pores are configured to interact with the light emission from the luminescence donor to provide a measurable light emission which is indicative of the presence of the matrix metalloproteinase;

contacting the surface of the optical biosensor with a sample of the in cancer tissue or blood to allow interaction of the matrix metalloproteinase (if present) and the linker;

detecting a change in light emission from the optical biosensor, and using the detected change in light emission to provide an indication of cancer status.

In certain embodiments, the biosensor further comprises a bioanalyte specific capture agent. The bioanalyte specific capture agent may comprise a binding agent capable of selectively binding a specific MMP protein selected from one of the group consisting of MMP-1, -2, -3 and -9. The binding agent may be capable of selectively binding the one selected MMP in the presence of the other listed MMPs. The binding agent may be an antibody. The binding agent may be functionalised magnetic nanoparticles (MNPs) having the antibody bound to a surface thereof.

In certain other embodiments, the bioanalyte is a bacterial biomarker. Accordingly, in a sixth aspect there is provided a method for monitoring and/or assessing bacterial infection in a subject, the method comprising:

providing an optical biosensor for detecting a bacterial biomarker in a body fluid from said subject, the biosensor comprising: a porous silicon or alumina substrate comprising a surface and a detection agent immobilised on the surface, the detection agent comprising a sensing domain and a signaling domain, the sensing domain comprising a linker that is a substrate for the bacterial biomarker and the signaling domain comprising a luminescence donor and a luminescence acceptor wherein the luminescence donor and the luminescence acceptor are connected by the linker and are optically coupled such that emission of light from the luminescence donor is substantially quenched by the luminescence acceptor, and interaction of the bacterial biomarker with the linker results in cleavage of the linker and optical un-coupling of the luminescence donor and the luminescence acceptor to thereby result in light emission from the luminescence donor, and a plurality of light interacting pores on the surface of the substrate, wherein the pores are configured to interact with the light emission from the luminescence donor to provide a measurable light emission which is indicative of the presence of bacterial biomarker;

contacting the surface of the optical biosensor with a sample of the body fluid to allow interaction of the bacterial biomarker (if present) and the linker;

detecting a change in light emission from the optical biosensor; and using the detected change in light emission to provide an indication of bacterial infection.

The bacterial biomarker may be used as an indicator of wound status in a subject. Accordingly, in a seventh aspect there is provided a method for monitoring and/or assessing wound status in a subject, the method comprising:

providing an optical biosensor for detecting a bacterial biomarker in a wound fluid from said subject, the biosensor comprising: a porous silicon or alumina substrate comprising a surface and a detection agent immobilised on the surface, the detection agent comprising a sensing domain and a signaling domain, the sensing domain comprising a linker that is a substrate for the bacterial biomarker and the signaling domain comprising a luminescence donor and a luminescence acceptor wherein the luminescence donor and the luminescence acceptor are connected by the linker and are optically coupled such that emission of light from the luminescence donor is substantially quenched by the luminescence acceptor, and interaction of the bacterial biomarker with the linker results in cleavage of the linker and optical un-coupling of the luminescence donor and the luminescence acceptor to thereby result in light emission from the luminescence donor, and a plurality of light interacting pores on the surface of the substrate, wherein the pores are configured to interact with the light emission from the luminescence donor to provide a measurable light emission which is indicative of the presence of bacterial biomarker;

contacting the surface of the optical biosensor with a sample of the wound fluid to allow interaction of the bacterial biomarker (if present) and the linker;

detecting a change in light emission from the optical biosensor; and using the detected change in light emission to provide an indication of wound status.

In certain embodiments of the fourth to seventh aspects, the change in light emission may be any one of a change in the wavelength of the light emitted and/or a change in the intensity of the light emitted from the optical biosensor.

In certain embodiments of the fifth to seventh aspects, the biosensor further comprises a bioanalyte specific capture agent. The bioanalyte specific capture agent may comprise a binding agent capable of selectively binding the bacterial biomarker. The binding agent may be an antibody. The binding agent may be functionalised magnetic nanoparticles (MNPs) having the antibody bound to a surface thereof.

The bacterial biomarker of the fifth and seventh aspects may be a peptide, protein or other molecule that is indicative of infection by a bacterial species such as *Bacillus anthracis, Bacillus cereus, Staphylococcus aureus, Listeria monocytogenes, Streptococcus pneumoniae, Streptococcus pyogenes, Clostridium botulinum, Clostridium difficile, Clostridium perfringens, Clostridium tetani, Borrelia burgdorferi, Treponema pallidum, Chlamydia trachomatis, Chlamydophila psittaci, Corynebacterium diphtherias, Mycobacterium tuberculosis,* and *Mycobacterium avium, Rickettsia prowazekii, Rickettsia rickettsii, Rickettsia typhi, Anaplasma phagocytophilum, Ehrlichia chaffeensis, Brucella melitensis, Bordetella pertussis, Burkholderia mallei, B. pseudomallei, Neisseria gonorrhoeae, Neisseria meningitides, Campylobacter jejuni, Helicobacter pylori, Legionella pneumophila, Acinetobacter baumannii, Moraxella catarrhalis, Pseudomonas aeruginosa, Aeromonas* sp., *Vibrio cholerae, Vibrio parahaemolyticus, Thiotrichales* sp., *Haemophilus influenzae, Klebsiella pneumoniae, Proteus mirabilis, Yersinia pestis, Yersinia enterocolitica, Shigella flexneri, Salmonella enterica* or *Escherichia coli.*

In certain embodiments of the first to seventh aspects, the optical biosensor is part of a detection device. In these embodiments, the detection device may be a point-of-care (POC) device. The detection device comprises a fluid inlet through which the sample can be introduced, the optical biosensor described herein, and an optical output for outputting information on the emission intensity of the luminescence donor.

The detection device may also comprise a means for directly collecting and transferring a test sample from a subject to the detection device. Specifically, the detection device may utilise a microneedle or one or more microneedle arrays designed to transfer a bodily fluid, such as a wound fluid, from the subject to the device via capillary action and/or surface tension.

The detection device may be used for detection of multiple target bioanalytes. Thus, the housing may comprise a plurality of spatially arranged optical biosensors with each biosensor comprising detection agents specific to different bioanalytes so that each biosensor is capable of selectively detecting a different bioanalyte relative to an adjacent biosensor. For example, each biosensor may be capable of detecting a bioanalyte that is indicative of a specific bacterial species and the detection device can thereby be used in the detection of a plurality of bacterial infections in a single step. In these embodiments, each biosensor may have the same luminescence donor and acceptor pair but different linkers. Alternatively, a single or multiple biosensors may comprise detection agents having the same linker but each having different luminescence donor and acceptor pairs.

In certain other embodiments, the optical biosensor may be part of a wound dressing or bandage. In these embodiments, the optical biosensor may be fixed or otherwise attached to a wound dressing or bandage material and may provide information to a practitioner regarding the status of a wound.

The optical biosensor described herein could be part of a theranostic device. Thus, in an eighth aspect there is provided a theranostic device for the diagnosis and/or treatment of a disease or pathological condition in a subject, the device comprising:

providing an optical biosensor for detecting and/or determining the concentration of a bioanalyte that is a biomarker of said disease or pathological condition in a sample of bodily fluid obtained from said subject, the optical biosensor comprising: a porous silicon or alumina substrate comprising a surface and a detection agent immobilised on the surface, the detection agent comprising a sensing domain and a signaling domain, the sensing domain comprising a linker capable of interacting with the target bioanalyte and the signaling domain comprising a luminescence donor and a luminescence acceptor wherein the luminescence donor and the luminescence acceptor are connected by the linker and are optically coupled such that emission of light from the luminescence donor is substantially quenched by the luminescence acceptor, and interaction of the target bioanalyte with the linker results in optical un-coupling of the luminescence donor and the luminescence acceptor to thereby result in light emission from the luminescence donor, and a plurality of light interacting pores on the surface of the substrate, wherein the pores are configured to interact with the light emission from the luminescence donor to provide a measurable light emission which is indicative of the presence of the target bioanalyte;

a detector for detecting a change in light emission from the optical biosensor and providing an output signal containing information on said change in light emission;

a delivery system for delivering a therapeutic agent to the subject; and a controller for processing the output signal from the detector and activating the delivery system as required based on information obtained from the output signal.

In certain embodiments of the eighth aspect, the biosensor further comprises a bioanalyte specific capture agent. The bioanalyte specific capture agent may comprise a binding agent capable of selectively binding the bioanalyte. The binding agent may be an antibody. The binding agent may be functionalised magnetic nanoparticles (MNPs) having the antibody bound to a surface thereof.

As described previously, the measurable light emission is advantageously enhanced or amplified relative to the light emission that would be measured in the absence of the light interacting pores on the surface of the substrate.

BRIEF DESCRIPTION OF THE FIGURES

Embodiments of the present invention will be discussed with reference to the accompanying figures wherein.

DESCRIPTION OF EMBODIMENTS

Figure 1:
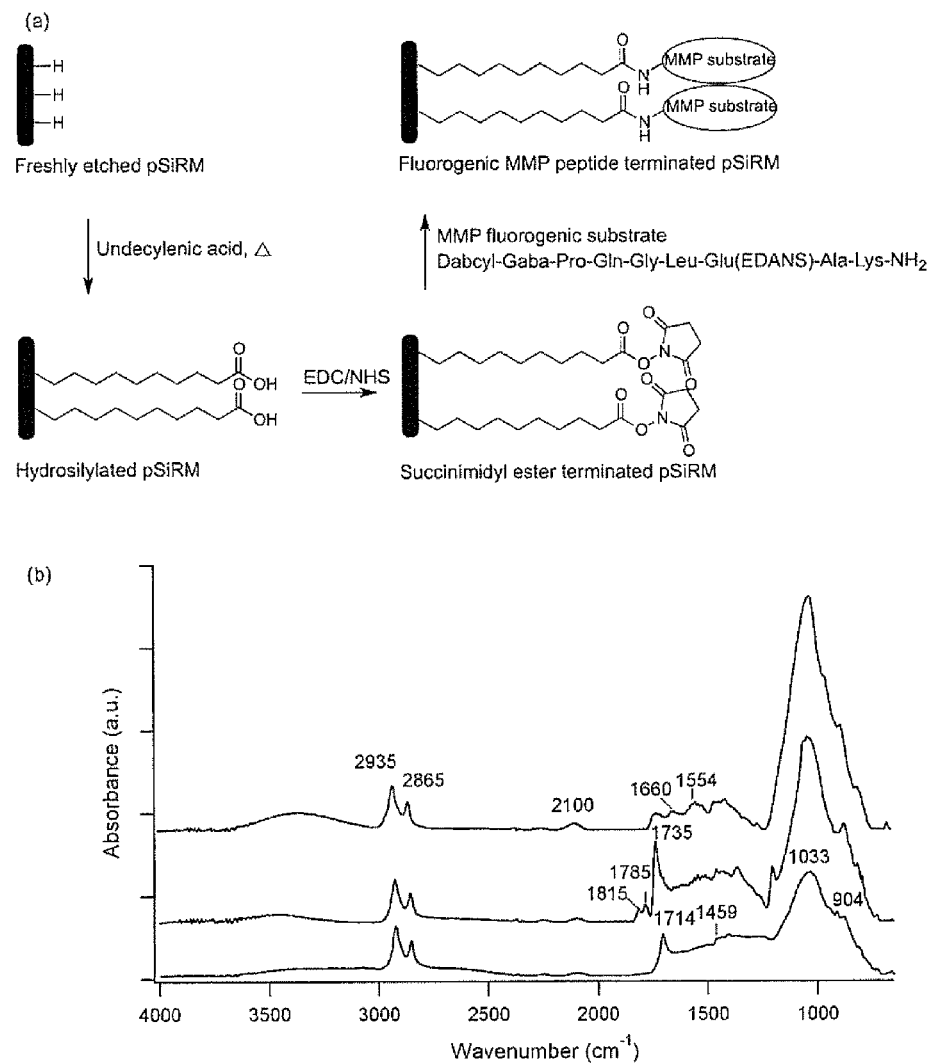
FIG. 1 shows: (a) a schematic representation of surface functionalisation reactions of a hydride-terminated porous silicon resonance microcavity (pSiRM) surface involving hydrosilylation with undecylenic acid, NHS ester formation and reaction with fluorogenic matrix metalloproteinase (MMP) substrate; and (b) baseline-corrected FTIR-ATR spectra of the pSiRM surface (i) after hydrosilylation with undecylenic acid, (ii) activation with EDC/NHS and (iii) immobilisation of the fluorogenic MMP peptide substrate.

Disclosed herein is an optical biosensor for detecting a target bioanalyte in a sample. The biosensor comprises a porous silicon or alumina substrate comprising a surface and a detection agent immobilised on the surface. The detection agent comprises a sensing domain and a signaling domain. The sensing domain comprises a linker capable of interacting with the target bioanalyte and the signaling domain comprises a luminescence donor and a luminescence acceptor. The luminescence donor and the luminescence acceptor are connected by the linker and are optically coupled in the absence of the target bioanalyte such that emission of light from the luminescence donor is substantially quenched by the luminescence acceptor. Interaction of the target bioanalyte with the linker results in optical un-coupling of the luminescence donor and the luminescence acceptor to thereby result in light emission from the luminescence donor. The surface of the substrate further comprises a plurality of light interacting pores, wherein the pores are configured to interact with the light emission from the luminescence donor to provide a measurable light emission which is indicative of the presence of the target bioanalyte.

In embodiments, the light emission from the luminescence donor is enhanced by interaction with the light interacting pores of the substrate. An internal surface of the light interacting pores may comprise an optical structure that interacts with the light emission from the luminescence donor. The optical structure may be an optical filter, reflector or cavity. The internal surface of the light interacting pores may comprise a Bragg reflector, a rugate filter, a resonant microcavity, or a combination of any of these optical features.

For ease of discussion, further reference will now be made to a substrate that is a porous silicon resonant microcavity (pSiRM) substrate in which the light interacting pores comprise distributed Bragg reflectors separated by a resonant microcavity. However, it will be appreciated that aspects of the discussion apply to other embodiments in which the light interacting pores comprise another type of optical feature, such as a rugate filter, a resonant microcavity or a Bragg reflector.

Furthermore, further reference will be made to luminescence donors and the luminescence acceptors that are fluorescence donors and fluorescence acceptors. It will be appreciated that the luminescence donors and the luminescence acceptors could be phosphorescence donors and phosphorescence acceptors and that aspect of the further discussion apply to these embodiments as well.

In particular, specific embodiments provide a real-time, sensitive and selective detection device to monitor the healing status of chronic wounds at the point of care. The photonic properties of porous silicon resonant microcavity (pSiRM) provide an optical biosensor to monitor the presence of specific biomarkers found in wound exudate, such as matrix metalloproteinases (MMPs) and bacterial enzyme biomarkers. In embodiments, the pSiRM is functionalised using a fluorogenic MMP peptide substrate featuring both a fluorophore and a quencher. The peptide-functionalised pSiRM is then used as a fluorescence-based optical biosensor for MMPs. Active MMPs interact with and cleave the linker, producing an immobilised peptide fragment carrying the fluorophore. The fluorescence intensity of the fluorophore embedded within the pSiRM matrix is enhanced by the photonic structure of the pSiRM compared to other pSi photonic structures. This fluorescence enhancement translates into high sensitivity, enabling detection of MMP-1 at a limit of detection as low as $7.5 \times 10^{-19}$ M after only 15 min incubation time.

The biosensor comprises a porous silicon resonant microcavity (pSiRM) substrate. Porous silicon (pSi) has been used previously in optical biosensors. For example, Gao et al.[20] achieved MMP-2 detection as low as $1.5 \times 10^{-12}$ M using a biosensor based on a pSi rugate filter coated with gelatin, which can be digested by MMP-2. The digestion products then entered in to the pSi matrix and induced color changes that could be observed by the naked eye. Martin et al.[21] designed a biosensor to detect MMP-8 based on antibody-functionalised pSiRM and monitored the presence of MMP-8 by observing a shift in the resonance cavity dip of the pSiRM. This device was able to detect MMP-8 down to $1.5 \times 10^{-9}$ M. However, neither of these biosensors was used with complex biological fluids. Kilian et al.[22] developed a label-free biosensor to detect MMPs secreted by human macrophages as an example of a biological fluid. The biosensor was based on photonic crystals of anodized silicon loaded with a biopolymer. It successfully detected MMP-9 down to a level of $1.2 \times 10^{-12}$ M. In our previous study, we developed an optical biosensor based on single layer pSi functionalised with a synthetic MMP inhibitor and demonstrated that the biosensor selectively detected the MMPs in wound fluid sample at physiologically relevant concentrations of MMPs found in chronic wound fluid.[23]

Alternatively, the substrate may be a porous alumina substrate.

The pSiRM is a photonic structure comprising two distributed Bragg reflectors (DBR) separated by a microcavity layer, producing a reflectance spectrum with a sharp resonance cavity dip in the center of the reflectance band.[32-34] Each DBR consists of periodic layers of alternating low porosity (LP) and high porosity (HP) pSi, with high and low refractive index, respectively, but the same optical thickness. The optical thickness for each DBR is ¼, where 1 is the central wavelength of the photonic resonance band with near 100% reflectance. The resonance microcavity has an optical thickness of an integer multiple of ½. The position of the central wavelength of the resonance cavity dip can be tuned by changing the electrochemical etching parameters.[35]

The pSiRM substrate can be formed by electrochemical etching. For example, pSiRM substrates can be fabricated by anodically etching a Si wafer using a current density alternating between 50 mA/cm$^2$ for 2288 ms and 25 mA/cm$^2$ for 1820 ms to form HP and LP layers, respectively. The resonant microcavity can be etched at a current density of 50 mA/cm$^2$ for 9152 ms. The resulting pSiRM had the configuration $(HP/LP)_3(HP)_4(LP/HP)_3$. The Si wafer may be pre-treated in order to remove the parasitic layer from the substrate prior to the electrochemical etching.

pSi substrates have many advantages when used in label-free optical biosensors. Specifically, pSi substrates have a very large surface area (up to 600 m$^2$/g), tunable morphological and optical properties, they are biocompatible and have a range of surface chemistries. Pore size can be tuned to allow ingress of even large biomolecules such as antibodies. Advantageously, the morphological properties such as pore size, porosity and thickness can be tuned to fabricate pSi substrates suitable for ingress of the targeted bioanalyte while excluding others.

Biocompatibility of the substrate material is also essential when direct contact of the biosensor occurs with the human body, such as through a smart dressing. pSi is well tolerated in vitro and in vivo and degrades into orthosilicic acid, the natural form of silicon in humans.

The pSiRM substrates described herein have two interesting optical features for biosensing applications. Firstly, the resonance cavity dip of the pSiRM is sensitive to the refractive index changes. Specifically, small refractive index changes induce large shifts in the optical spectrum. This optical feature lends itself to biosensor design and has been previously explored in biosensing applications, such as glucose detection,[35] bacteria detection,[33, 41] viruses and DNA detection.[42] The second optical feature is a confinement effect of light inside the microcavity to a specific wavelength contributing to the enhancement of fluorescence emission of the fluorescence donor immobilised on the pSiRM. The optimum enhancement of the fluorescence emission is obtained if the wavelength of the microcavity dip is aligned with the emission wavelength of the fluorescence donor.

The surface of freshly etched pSiRM substrates may be unstable and prone to oxidation in the presence of oxygen or to hydrolysis in the presence of water leading to uncontrollable optical properties which is undesirable for biosensor applications. To overcome this, the surface of the freshly etched pSiRM substrate may be functionalised. The surface may be functionalised with an alkylating agent to produce a functionalised alkyl monolayer on the surface of the substrate, or by surface modification with alkenes, yielding organic monolayers covalently attached to the surface[66] or by grafting of alkynes to the hydride-terminated silicon surface through a direct Si—C bond via nanoscale cathodic electrografting reaction through the use of conducting atomic force microscope (ATM).[67]

In embodiments, the surface of the freshly etched substrate is functionalised with an alkylating agent. The alkylating agent may be an alkyl carboxylic acid, such as a $C_5$-$C_{20}$ carboxylic acid, ester, suphonate, alkyne, azide, alkene, or combination of any of the aforementioned. In specific embodiments, the surface is hydrosilylated using undecylenic acid. This produces a dense alkyl monolayer with stable Si—C bonds protecting the pSiRM surface from oxidative hydrolysis.

The functional group on the alkylating agent can be used to covalently attach the detection agent. For example, a carboxylic acid can be used to covalently attach the detection agent using known peptide synthesis methods. Thus, a carboxylic acid-terminated surface can be activated to form an NHS ester-terminated surface by reacting the pSiRM samples with N-hydroxysuccinimide (NHS) in the presence of a coupling agent, such as 1-(3-dimethylaminopropyl)-3-ethylcarbodiimide (EDC). The detection agent can then be coupled to the NHS ester-terminated surface by reacting the functionalised pSiRM surface with the detection agent to provide a modified pSiRM surface that is ready for use in biosensing.

The detection agent may be a fusion peptide or protein comprising a signaling domain and a sensing domain. The signaling domain comprises a fluorescence donor and a fluorescence acceptor. The sensing domain comprises a bioanalyte-binding peptide. The fluorescence donor and the fluorescence acceptor are fused to both termini of the bioanalyte-binding peptide. The fluorescence donor and/or the fluorescence acceptor may be fused to the bioanalyte-binding peptide or protein via a linker.

The fluorescence donor and the fluorescence acceptor are connected by the linker and are optically coupled in the absence of the target bioanalyte such that emission of light from the fluorescence donor is substantially quenched by the fluorescence acceptor via fluorescence resonance energy transfer ("FRET"). FRET is a non-radiative energy transfer between two fluorophores having different emission wavelengths, in which the excitation energy of a fluorescence donor in an excited state is transferred to a fluorescence acceptor and quenching of the fluorescence donor is observed.[68]

As used herein, the term "fluorescence donor" means a fluorophore acting as a donor in the FRET mechanism, and the term "fluorescence acceptor" refers to a fluorophore acting as an acceptor in the FRET mechanism. The fluorescence donor can be any dye molecule that absorbs light which places the dye in an excited state and then returns to the ground state by emitting light (fluorescence). The fluorescence acceptor can be any dye molecule with no native fluorescence which nonradiatively accepts energy from the fluorescence donor to generate an acceptor excited state. The fluorescence acceptor then preferably returns to the ground state nonradiatively by giving off energy as heat.

The energy transfer efficiency of FRET varies depending on the range in which the emission spectrum of the fluorescence donor and the absorption spectrum of the fluorescence acceptor overlap with each other, the quantum efficiency of the fluorescence donor, the relative orientation of transition dipoles of the fluorescence donor and the fluorescence acceptor, and the distance between the fluorescence donor and the fluorescence acceptor. Thus, the energy transfer efficiency of FRET varies depending on the distance between the fluorescence donor and the fluorescence acceptor and the relative orientation thereof.

Any fluorescence donor and fluorescence acceptor pair for which the emission spectrum of the donor and the absorption spectrum of the acceptor can overlap with each other to cause FRET may be used. Examples of fluorescence donors that may be used include fluorescent proteins, fluorescent dyes, bioluminescent proteins, and quantum dots, which have various wavelengths. Examples of fluorescence acceptors that may be used include fluorescent proteins, fluorescent dyes, and quantum dots, which have wavelengths different from those of the fluorescence donor. Alternatively, the fluorescence acceptor may consist of quenchers or gold nanoparticles, which reduce the fluorescence intensity of the fluorescence donor.

5-[(2-Aminoethyl)amino]naphthalene-1-sulfonic acid (EDANS) is a common fluorescence donor for use in FRET-based systems. EDANS can be paired with the fluorescence acceptors 4-((4-(dimethylamino)phenyl)azo)benzoic acid (Dabcyl) or 4-((4-(dimethylamino)phenyl)azo)sulfonic acid (Dabsyl). Other FRET pairs that may be used include: ECFP (enhanced cyan fluorescent protein) and EYFP (enhanced yellow fluorescent protein), which are fluorescent proteins acting as a fluorescence donor and a fluorescence acceptor, respectively; fluorescein and Dabcyl acting as a fluorescence donor and a fluorescence acceptor, respectively; fluorescein and Cy5 acting as a fluorescence donor and a fluorescence acceptor, respectively; gold nanoparticles and Cy3 acting as a fluorescence donor and a fluorescence acceptor, respectively; or gold nanoparticles and Cy5 acting as a fluorescence donor and a fluorescence acceptor, respectively.

Alternatively, the fluorescence donor and fluorescence acceptor pair may be colloidal semiconductor nanocrystals (ie. quantum dots). The broad absorption spectra of quantum dots allow flexibility in choosing the desired excitation wavelength where direct excitation of the acceptor molecules can be substantially reduced. For example, luminescent CdSe—ZnS core-shell quantum dots (QDs) may be used as the fluorescence donor in conjunction with any of the fluorescence acceptors described above, such as Cy3. The detection agent can be prepared by conjugating the fluorescence acceptor with the bioanalyte-binding peptide and then allowing the product to self-assemble on appropriately functionalised quantum dots (eg. quantum dots functionalised with a dithiol-alkyl-COOH ligands). The methods described in Clapp et al. can be used to prepare detection agents based on quantum dots.[70]

The sensing domain links the fluorescence donor and the fluorescence acceptor and comprises a bioanalyte-binding domain. The bioanalyte-binding domain may be a peptide, protein, sugar, amino acid, lipid or other agent that selectively binds the bioanalyte and undergoes a conformational or compositional change as a result of that binding.

A conformational change in the bioanalyte-binding domain may result from the bioanalyte competitively binding to a domain that is otherwise intermolecularly bound to another portion of the domain in the absence of the bioanalyte (i.e. unfolding of the bioanalyte-binding domain). However, in the presence of the bioanalyte, the intramolecular binding is reduced, thereby resulting in the fluorescence donor and the fluorescence acceptor spatially separating from one another to give a measurable fluorescence emission.

Alternatively, the bioanalyte-binding domain undergoes a compositional change when it interacts with the bioanalyte. The bioanalyte may be a protease enzyme and the bioanalyte-binding domain may be a peptide or protein that is a substrate for the enzyme.

Optionally, to assist in selectively binding a target bioanalyte from complex fluids or similar that contain other components that are structurally or functionally related to the target bioanalyte and may competitively bind to the sensing domain of the detection agent, the biosensor may further comprise a bioanalyte specific capture agent.

The bioanalyte specific capture agent may comprise a binding agent capable of selectively binding the target bioanalyte. The bioanalyte specific capture agent may be deposited on or near the surface of the porous silicon or alumina substrate so that at least some of any bioanalyte captured by the capture agent is capable of interacting with the sensing domain of the detection agent.

The bioanalyte specific capture agent may be in the form of particles comprising a binding agent on the surface thereof. For example, the particles may be functionalised nanoparticles (NPs) having the binding agent bound to a surface thereof. The functionalised NPs may interact with and be retained on the surface of the substrate. For example, the functionalised NPs may be functionalised magnetic nanoparticles (MNPs).

The binding agent may be any agent that selectively binds the target bioanalyte. The binding agent may bind the target bioanalyte selectively from complex fluids comprising other components that are structurally related to the target bioanalyte. For example, the biding agent may be an antibody. The biosensor of these embodiments may be used for the selective detection of a specific peptide or protein in a family of structurally related peptides or proteins.

In embodiments, the bioanalyte is a matrix metalloproteinase (MMP) (described in detail later) and the bioanalyte-binding domain of the detection agent is a substrate for the MMP. In these embodiments, the bioanalyte-binding domain may comprise the MMP substrate [Gaba-Pro-Gln-Gly-Leu-Glu-Ala-Lys-NH$_2$] (SEQ ID NO: 1) in which case the detection agent may be [Dabcyl-Gaba-Pro-Gln-Gly-Leu-Glu(EDANS)-Ala-Lys-NH$_2$] SEQ ID NO: 2). In these embodiments, the distance between Dabcyl and EDANS is about 5-6 nm, at which FRET can occur. Thus, when EDANS is excited at 335 nm, the excitation emission energy of EDANS is transferred to Dabcyl and then to heat. When the MMP cleaves the substrate peptide, the distance and relative orientation of EDANS and Dabcyl changes, resulting in a difference in FRET efficiency between them, and an increase in fluorescent emission from the EDANS. Thus, MMP can be sensed by measuring the change in emissions from the EDANS, and thus the MMP concentration can be quantitatively measured because the change increase in light emissions from the EDANS is in proportion to the MMP concentration.

A range of bioanalytes can be detected using the optical biosensor described herein. The bioanalyte is a biological molecule of interest in a sample that is to be detected, analysed, and/or quantified. Examples of bioanalytes include, but are not limited to, amino acids, peptides, polypeptides, proteins, glycoproteins, lipoproteins, nucleosides, nucleotides, oligonucleotides, nucleic acids, sugars, carbohydrates, oligosaccharides, polysaccharides, fatty acids, lipids, hormones, metabolites, cytokines, chemokines, receptors, neurotransmitters, antigens, allergens, antibodies, substrates, metabolites, cofactors, inhibitors, drugs, pharmaceuticals, nutrients, prions, toxins, poisons, explosives, pesticides, biohazardous agents, carcinogens, mutagens, narcotics, amphetamines, barbiturates, and hallucinogens.

Accurate monitoring of bioanalyte levels in subjects can be vital to the subject's health. For example, monitoring of glucose levels in diabetic subjects.

In embodiments, the bioanalyte is a peptide or protein associated with wounds. Management of chronic wounds in particular is challenging due to the complexity of the biochemical processes occurring in these wounds. Given the complexity of wound healing and the wound exudate matrix, a plethora of molecules have been identified as wound biomarkers, as listed by Harding et al.[1]

A clinically validated biomarker in chronic wounds is in the group of matrix metalloproteinases (MMPs).[1, 2, 10, 11] MMPs are proteolytic enzymes involved in the extracellular matrix (ECM) degradation and tissue remodeling processes during wound healing.[11-13] There are more than 20 MMPs which contain at least ~20 amino acid residue long signal peptides.[12] In general, MMPs can be classified into five groups based on their structural and functional properties. Those are the collagenases (such as MMP-1 and MMP-8); the gelatinases (including gelatinase-A or MMP-2); the stromelysins (such as stromelysin-1 or MMP-3); the membrane-type MMPs (such as MT1-MMP or MMP-14) and the heterogeneous subgroup containing matrilysin (MMP-7), enamelysin (MMP-20) and macrophage metalloelastase (MMP-12).[12, 14, 15] For example, the presence of MMP-9 in a wound sample may be indicative of a poor healing wound whilst the presence of MMP-8 may be indicative of good healing since the presence of MMP-8 is required for wound closure.

The activity of MMPs can be inhibited by tissue inhibitors of metalloproteinases (TIMPs)[12, 14-17] or synthetic inhibitors.[12, 16] The inhibition involves forming a chelate complex between TIMPs and a zinc ion at the active site of MMP.[11, 16] This affords possibilities for therapeutic intervention by administration of synthetic MMP inhibitors to maintain the level of MMPs and promote wound healing.[11, 18] However, the concentration of MMPs needs to be known to correctly dose the inhibitor since over-inhibition is also deleterious.[11] Therefore, chronic wound management would benefit from a POC biosensor that is able to rapidly establish MMP levels in wound fluid.

Accordingly, there is also provided a method for monitoring and/or assessing wound status in a subject, the method comprising:

providing an optical biosensor for detecting a matrix metalloproteinase in a wound fluid from said subject, the biosensor comprising: a porous silicon or alumina substrate comprising a surface and a detection agent immobilised on the surface, the detection agent comprising a sensing domain and a signaling domain, the sensing domain comprising a linker that is a substrate for the matrix metalloproteinase and the signaling domain comprising a luminescence donor and a luminescence acceptor wherein the luminescence donor and the luminescence acceptor are connected by the linker and are optically coupled such that emission of light from the luminescence donor is substantially quenched by the luminescence acceptor, and interaction of the matrix metalloproteinase with the linker results in cleavage of the linker and optical un-coupling of the luminescence donor and the luminescence acceptor to thereby result in light emission from the luminescence donor, and a plurality of light interacting pores on the surface of the substrate, wherein the pores are configured to interact with the light emission from the luminescence donor to provide a measurable light emission which is indicative of the presence of the matrix metalloproteinase;

contacting the surface of the optical biosensor with a sample of the wound fluid to allow interaction of the matrix metalloproteinase (if present) and the linker, detecting a change in light emission from the optical biosensor; and using the detected change in light emission to provide an indication of wound status.

In specific embodiments, the substrate is a porous silicon resonant microcavity (pSiRM) substrate and there is provided a method for monitoring and/or assessing wound status in a subject, the method comprising:

providing an optical biosensor for detecting a matrix metalloproteinase in a wound fluid from said subject, the biosensor comprising: a porous silicon resonant microcavity (pSiRM) substrate comprising a surface comprising a plurality of light interacting pores, each pore comprising distributed Bragg reflectors separated by a microcavity; and a detection agent immobilised on the surface, the detection agent comprising a sensing domain and a signaling domain, the sensing domain comprising a linker that is a substrate for the matrix metalloproteinase and the signaling domain comprising a fluorescence donor and a fluorescence acceptor wherein the fluorescence donor and the fluorescence acceptor are connected by the linker and are optically coupled such that emission of light from the fluorescence donor is substantially quenched by the fluorescence acceptor, and interaction of the matrix metalloproteinase with the linker results in cleavage of the linker and optical un-coupling of the fluorescence donor and the fluorescence acceptor to thereby give a measurable emission from the fluorescence donor which is indicative of the presence of the matrix metalloproteinase, wherein said emission is enhanced by interaction with the light interacting pores of the substrate;

contacting the surface of the optical biosensor with a sample of the wound fluid to allow interaction of the matrix metalloproteinase (if present) and the linker, detecting light emission from the fluorescence donor; and using the detected light emission to provide an indication of wound status.

MMPs assays already exist, but they have not been developed and demonstrated for chronic wounds.[19-21] For example, Beekman et aL[19] synthesised a soluble and selective fluorogenic peptide substrate TNO211 [Dabcyl-Gaba-Pro-Gln-Gly-Leu-Glu(EDANS)-Ala-Lys-NH$_2$] (SEQ ID NO: 2) containing an MMP cleavable peptide sequence (Gly-Leu) and a pair of EDANS (5-((2-aminoethyl)amino) naphthalene-1-sulfonic acid) and Dabcyl (4-(4-dimethylaminophenylazo)benzoyl) as fluorophore and quencher, respectively. Using this substrate, they were able to detect MMPs in complex samples, such as a culture media and synovial fluid.[19] This particular peptide substrate is now commercially available (produced by Merck and known as MMP substrate III, fluorogenic).

The selectivity of the biosensor toward specific MMPS may be achieved using a bioanalyte specific capture agent.

The bioanalyte specific capture agent may comprise a binding agent capable of selectively binding a specific MMP protein, such as one selected from one of the group consisting of MMP-1, -2, -3 and -9. The binding agent may be capable of selectively binding the one selected MMP in the presence of other MMPs. The binding agent may be an antibody.

The binding agent may be functionalised nanoparticles (NPs), such as functionalised magnetic nanoparticles (MNPs), having the antibody bound to a surface thereof. NPs are functionalised with the MMP antibody (MMPAb) to harvest the target MMP from buffer solution or from wound fluid samples. The NPs can be modified with any type of MMPAb depending on the targeted MMP. For example, the MNPs are immobilised with MMP-1Ab in order to target MMP-1.

The size of the functionalised NPs may facilitate an easy infiltration of nanoparticles throughout the porous layer of the porous silicon or alumina substrate.

MMPs have also been strongly implicated in multiple stages of cancer progression including the acquisition of invasive and metastatic properties.[71] Accordingly, there is provided a method for monitoring and/or assessing cancer status in a subject, the method comprising:
   providing an optical biosensor for detecting a matrix metalloproteinase in cancer tissue or blood from said subject, the biosensor comprising: a porous silicon or alumina substrate comprising a surface and a detection agent immobilised on the surface, the detection agent comprising a sensing domain and a signaling domain, the sensing domain comprising a linker that is a substrate for the matrix metalloproteinase and the signaling domain comprising a luminescence donor and a luminescence acceptor wherein the luminescence donor and the luminescence acceptor are connected by the linker and are optically coupled such that emission of light from the luminescence donor is substantially quenched by the luminescence acceptor, and interaction of the matrix metalloproteinase with the linker results in cleavage of the linker and optical un-coupling of the luminescence donor and the luminescence acceptor to thereby result in light emission from the luminescence donor, and a plurality of light interacting pores on the surface of the substrate, wherein the pores are configured to interact with the light emission from the luminescence donor to provide a measurable light emission which is indicative of the presence of the matrix metalloproteinase;
   contacting the surface of the optical biosensor with a sample of the in cancer tissue or blood to allow interaction of the matrix metalloproteinase (if present) and the linker,
   detecting a change in light emission from the optical biosensor; and
   using the detected change in light emission to provide an indication of cancer status.

The cancer tissue or blood can be obtained from a subject using known techniques, such as biopsy.

In certain other embodiments, the bioanalyte is a bacterial biomarker. Accordingly, there is provided a method for monitoring and/or assessing bacterial infection in a subject, the method comprising:
   providing an optical biosensor for detecting a bacterial biomarker in a body fluid from said subject, the biosensor comprising: a porous silicon or alumina substrate comprising a surface and a detection agent immobilised on the surface, the detection agent comprising a sensing domain and a signaling domain, the sensing domain comprising a linker that is a substrate for the bacterial biomarker and the signaling domain comprising a luminescence donor and a luminescence acceptor wherein the luminescence donor and the luminescence acceptor are connected by the linker and are optically coupled such that emission of light from the luminescence donor is substantially quenched by the luminescence acceptor, and interaction of the bacterial biomarker with the linker results in cleavage of the linker and optical un-coupling of the luminescence donor and the luminescence acceptor to thereby result in light emission from the luminescence donor, and a plurality of light interacting pores on the surface of the substrate, wherein the pores are configured to interact with the light emission from the luminescence donor to provide a measurable light emission which is indicative of the presence of bacterial biomarker;
   contacting the surface of the optical biosensor with a sample of the body fluid to allow interaction of the bacterial biomarker (if present) and the linker;
   detecting a change in light emission from the optical biosensor; and
   using the detected change in light emission to provide an indication of bacterial infection.

The body fluid can be any fluid or tissue suspected of containing the bacterial biomarker of interest including, but not limited to, blood, wound fluid, sweat, saliva, excreta, body tissue and tissue fluids. The body fluid can be collected using known techniques.

In specific embodiments, the substrate is a porous silicon resonant microcavity (pSiRM) substrate and there is provided a method for monitoring and/or assessing wound status in a subject, the method comprising:
   providing an optical biosensor for detecting a bacterial biomarker in a wound fluid from said subject, the biosensor comprising: a porous silicon resonant microcavity (pSiRM) substrate comprising a surface comprising a plurality of light interacting pores, each pore comprising distributed Bragg reflectors separated by a microcavity; and a detection agent immobilised on the surface, the detection agent comprising a sensing domain and a signaling domain, the sensing domain comprising a linker that is a substrate for the bacterial biomarker and the signaling domain comprising a fluorescence donor and a fluorescence acceptor wherein the fluorescence donor and the fluorescence acceptor are connected by the linker and are optically coupled such that emission of light from the fluorescence donor is substantially quenched by the fluorescence acceptor, and interaction of the bacterial biomarker with the linker results in cleavage of the linker and optical un-coupling of the fluorescence donor and the fluorescence acceptor to thereby give a measurable emission from the fluorescence donor which is indicative of the presence of the bacterial biomarker, wherein said emission is enhanced by interaction with the light interacting pores of the substrate;
   contacting the surface of the optical biosensor with a sample of the wound fluid to allow interaction of the bacterial biomarker (if present) and the linker;
   detecting light emission from the fluorescence donor; and
   using the detected light emission to provide an indication of wound status.

The bacterial biomarker may be a peptide, protein or other molecule that is indicative of infection by a bacterial species such as *Bacillus anthracis, Bacillus cereus, Staphylococcus*

*aureus, Listeria monocytogenes, Streptococcus pneumoniae, Streptococcus pyogenes, Clostridium botulinum, Clostridium difficile, Clostridium perfringens, Clostridium tetani, Borrelia burgdorferi, Treponema pallidum, Chlamydia trachomatis, Chlamydophila psittaci, Corynebacterium diphtherias, Mycobacterium tuberculosis*, and *Mycobacterium avium, Rickettsia prowazekii, Rickettsia rickettsii, Rickettsia typhi, Anaplasma phagocytophilum, Ehrlichia chaffeensis, Brucella melitensis, Bordetella pertussis, Burkholderia mallei, B. pseudomallei, Neisseria gonorrhoeae, Neisseria meningitides, Campylobacter jejuni, Helicobacter pylori, Legionella pneumophila, Acinetobacter baumannii, Moraxella catarrhalis, Pseudomonas aeruginosa, Aeromonas* sp., *Vibrio cholerae, Vibrio parahaemolyticus, Thiotrichales* sp., *Haemophilus influenzae, Klebsiella pneumoniae, Proteus mirabilis, Yersinia pestis, Yersinia enterocolitica, Shigella flexneri, Salmonella enterica* or *Escherichia coli.*

Detection agents that are able to selectively detect any one of the aforementioned bacteria can be prepared using a suitable bioanalyte-binding peptide or protein and FRET pair, as described previously. For example, for the detection of *E. coli* the bioanalyte-binding peptide or protein may be MBP (maltose-binding protein), ALBP (allose-binding protein), ARBP (arabinose-binding protein) or GGBP (galactose/glucose-binding protein). For example, proteinase K is secreted by *Pseudomonas aeruginosa* and can digest polylysine. Therefore, a bioanalyte-binding peptide or protein comprising a poly-lysine motif can be used to detect *P. aeruginosa*. Hyaluronidase is secreted by *Staphylococcus aureus* and can digest hyaluronic acid. Therefore, a bioanalyte-binding peptide or protein comprising a hyaluronic acid motif can be used to detect *S. aureus*. However, any bioanalyte-binding peptide or protein may be used in the method and biosensor so long as it can undergo a conformational or compositional change as a result of binding of the bioanalyte thereto.

As used herein, the term "sample" refers to a composition that is suspected to contain the bioanalyte of interest and is to be analysed. The sample may comprise or be derived from a biological source such as a bodily fluid, including for example, wound fluid or exudate, blood, saliva, milk, mucous, urine, etc. Besides bodily fluids, other samples that may be tested include water samples and food and beverages products that may be monitored for toxins and/or contaminating pathogenic microorganisms. The sample may be collected from one or more of cells, water, soil, air, foods, waste, and animal and plant organs and tissues.

Routine methods well known by those of skill in the art may be used to obtain the sample.

Detection of the target bioanalyte in a sample is performed by measuring emissions from the fluorescence donor and the fluorescence acceptor using a fluorescence analysis system. Suitable fluorescence analysis systems include filter-type and monochrome-type fluorescence spectrophotometers. If a sample contains the target bioanalyte, changes in the emissions from the fluorescence donor and the fluorescence acceptor are sensed, whereby the target bioanalyte can be detected. Furthermore, if a change in the concentration of the target bioanalyte occurs, a change in the emissions from the fluorescence donor and the fluorescence acceptors occurs. Thus, the biosensor can be also be used to measure a change in the bioanalyte concentration.

Emissions from the fluorescence donor and the fluorescence acceptor can also be measured using a confocal microscope. For example, the detection agent can be spatially arranged on the substrate surface by microcontact printing and the emissions observed using confocal microscopy. This method can be used to form a multi-analyte biosensor.

In embodiments, the optical biosensor is part of a detection device. The detection device may be a point-of-care (POC) device. The detection device comprises a fluid inlet through which the sample can be introduced, a housing for the optical biosensor described herein, and an optical output for outputting information on the emission intensity of the fluorescence donor.

The detection device may also comprise a means for directly collecting and transferring a test sample from a subject to the detection device. Specifically, the detection device may utilise a microneedle or one or more microneedle arrays designed to transfer a bodily fluid, such as a wound exudate, from the subject to the device via capillary action and/or surface tension.

In embodiments, the optical biosensor may be part of a wound dressing or bandage. In these embodiments, the optical biosensor may be fixed or otherwise attached to a wound dressing or bandage material and may provide information to a practitioner regarding the status of a wound.

The bioassays described herein are designed to detect one or more bioanalytes of interest in a sample, the presence of which is correlated to a specific disease or predisposition to a disease. The presence of the bioanalytes of interest can function as a warning to a subject, or a healthcare professional, that a disease is present or may develop in the future.

The detection device may be used for detection of multiple target bioanalytes. Thus, the housing may comprise a plurality of spatially arranged optical biosensors with each biosensor capable of selectively detecting a different bioanalyte relative to an adjacent biosensor. For example, each biosensor may be capable of detecting a bioanalyte that is indicative of a specific bacterial species and the detection device can thereby be used in the detection of a plurality of bacterial infections in a single step.

In addition to diagnostics in human subjects, the methods and compositions of the invention may also have veterinary uses for diagnosing diseases in animals. Appropriate bioassays can be designed to selectively detect the intended target bioanalyte.

The optical biosensor described herein may be part of a theranostic device. As used herein, the term "theranostic" refers to a delivery system, which may be used to at least one of treating, preventing, monitoring or diagnosing a disease or pathological condition. Thus, provided herein is a theranostic device for the diagnosis and/or treatment of a disease or pathological condition in a subject, the device comprising:

providing an optical biosensor for detecting and/or determining the concentration of a bioanalyte that is a biomarker of said disease or pathological condition in a sample of bodily fluid obtained from said subject, the optical biosensor comprising: a porous silicon or alumina substrate comprising a surface and a detection agent immobilised on the surface, the detection agent comprising a sensing domain and a signaling domain, the sensing domain comprising a linker capable of interacting with the target bioanalyte and the signaling domain comprising a luminescence donor and a luminescence acceptor wherein the luminescence donor and the luminescence acceptor are connected by the linker and are optically coupled such that emission of light from the luminescence donor is substantially quenched by the luminescence acceptor, and interaction of the target bioanalyte with the linker results in optical un-coupling of the luminescence donor and the luminescence acceptor to thereby result in light emission from the luminescence donor, and a plurality of light interacting pores on the surface of the substrate, wherein the pores are configured to interact with the light emission from the luminescence donor to provide a measurable light emission which is indicative of the presence of the target bioanalyte;

a detector for detecting a change in light emission from the luminescence donor and providing an output signal containing information on said change in light emission;

a delivery system for delivering a therapeutic agent to the subject; and a controller for processing the output signal from the detector and activating the delivery system as required based on information obtained from the output signal.

As used herein, the term "pathological condition" means an abnormal anatomical or physiological condition and objective or subjective manifestations of disease, not classified as disease or syndrome.

A number of delivery systems may be used. For example, the delivery system may comprise a microparticle or a nanoparticle that is loaded with the therapeutic agent and is activated to release the therapeutic agent to treat the disease or pathological condition by the controller. The microparticle or nanoparticle can be a multistage particle, a porous particle, a porous silicon particle, a porous silica particle, a non-porous particle, a fabricated particle, a polymeric particle, a synthetic particle, a semiconducting particle, a virus, a gold particle, a silver particle, a quantum dot, an indium phosphate particle, an iron oxide particle, a micelle, a lipid particle, a liposome, a silica particle, a mesoporous silica particle, a PLGA-based particle, a gelatin-based particle, a carbon nanotube or a fullerene. The delivery system could also be a pump for delivering a liquid therapeutic agent to the subject.

Various therapeutic agents may be used. The therapeutic agent may be a physiologically or pharmacologically active substance that can produce a desired biological effect in a targeted site in an animal, such as a mammal or a human. The therapeutic agent may be any inorganic or organic compound. Examples include, without limitation, peptides, proteins, nucleic acids (including siRNA, miRNA and DNA), polymers, and small molecules.

Non-limiting examples of therapeutic agents include wound repair agents, tissue repair agents, thermal therapy agents, anti-bacterial agents, anti-inflammatory agents, anti-cancer agents, anti-proliferative agents, anti-vascularisation agents, and combinations thereof.

More specific but non-limiting examples of therapeutic agents include anti-infective agents; antibiotics, such as penicillins, cephalosporins, macrolids, tetracyclines, aminglycosides, and anti-tuberculosis agents; antifungal/antimycotic agents; antiviral agents, such as acyclovir, gancyclovir, ribavirin, anti-HIV agents, and anti-hepatitis agents; anti-inflammatory agents, such as NSAIDs, steroidal agents, cannabinoids; anti-allergic agents, such as antihistamines, (e.g., fexofenadine); vaccines or immunogenic agents, such as tetanus toxoid, reduced diphtheria toxoid, acellular pertussis vaccine, mumps vaccine, smallpox vaccine, anti-IIIV vaccines, hepatitis vaccines, pneumonia vaccines and influenza vaccines; anesthetics, including local anesthetics; antipyretics, such as paracetamol, ibuprofen, diclofenac, aspirin; agents for treatment of severe events, such as cardiovascular attacks, seizures, hypoglycemia; immunomodulators and immunostimulators; cardiovascular drugs, such as beta-blockers, alpha-blockers and calcium channel blockers; peptide and steroid hormones, such as insulin, insulin derivatives, insulin detemir, insulin monomeric, oxytocin, LHRH, LHRH analogues, adreno-corticotropic hormone, somatropin, leuprolide, calcitonin, parathyroid hormone, estrogens, testosterone, adrenal corticosteroids, megestrol, progesterone, sex hormones, growth hormones and growth factors; peptide and protein related drugs, such as amino acids, peptides, polypeptides and proteins; vitamins, such as Vitamin A, vitamins from the Vitamin B group, folic acid, Vitamin C, Vitamin D, Vitamin E, Vitamin K, niacin, and derivatives of Vitamins A-E; narcotics and antagonists, such as opiates and oxycodone; painkillers, such as opiates, endorphins, tramadol, codeine, NSAIDs and gabapentine.

EXAMPLES

We developed an optical biosensor based on the photonic structure of pSiRM functionalised using the fluorogenic MMP peptide substrate, [Dabcyl-Gaba-Pro-Gln-Gly-Leu-Glu(EDANS)-Ala-Lys-NH$_2$] (SEQ ID NO: 2). In the presence of MMPs, the peptide fragment carrying the quencher was cleaved off the surface, which allowed the EDANS fluorescence emission to be activated. In particular, we targeted MMP-1 as one of collagenases because this enzyme is one of key enzymes responsible for cleaving interstitial fibrillar collagen[44] which is crucial during wound healing.[45] We confirmed that the pSiRM structure afforded enhanced emission in comparison to other pSi structures and allowed detection of MMP-1 down to the attomolar level in buffer. This pSi optical biosensor was also successfully applied to detect MMPs in human wound fluid.

Materials

All chemical and reagents were purchased from Sigma-Aldrich unless otherwise stated. High purity solvents (methanol, ethanol, acetone and dichloromethane) were purchased from Chem Supply. All pSi samples were prepared from highly doped, (100)-oriented, phosphorus doped n-type Si wafer (0.008-0.02 Ωcm, Siltronix). The Si wafer was diced using a diamond cutter into pieces of 3-4 cm$^2$.

Example 1

Fabrication and Characterisation of Porous Silicon Resonance Microcavity Substrates pSi substrates were prepared in a Teflon-based electrochemical etching cell using aluminium tape as a contact for the silicon piece as anode and a platinum mesh as cathode. The electrochemical etching solution contained 25:200:1 volume ratio of aqueous hydrofluoric acid (48%, Scharlau)/water/surfactant (NCW1001, Wako Pure Chemical Industries).[36] The Si wafer was pre-treated in order to remove the parasitic layer from the substrate by anodically etching the Si wafer at a current density of 40 mA/cm$^2$ for 30 s, followed by a current density of 250 mA/cm$^2$ for 6 s which led to electropolishing. Following this step, the surface was exposed to MilliQ water for 1 min to remove the sacrificial layer, then rinsed with methanol, acetone, dichloromethane and dried under a stream of nitrogen gas.

The pre-treated Si wafer was then etched for 2 min at current densities specified in Table 1 to fabricate single layer pSi substrates used for fabrication of the porous silicon resonance microcavity ("pSiRM") substrates. The single layer pSi substrates were rinsed with methanol, acetone, dichloromethane and dried under a stream of nitrogen gas.

TABLE 1

The current density profile of single layer pSi etched at five different current densities

| Current density [mA/cm$^2$] | Etching time [s] | Pore diameter [nm] | Porosity [%] | Thickness [nm] | Etching rate [nm/s] |
|---|---|---|---|---|---|
| 25 | 120 | 40-60 | 67.0 | 3937 | 32.8 |
| 30 | 120 | 50-80 | 73.5 | 4066 | 33.9 |
| 40 | 120 | 80-110 | 77.7 | 4208 | 35.1 |
| 50 | 120 | 110-140 | 83.4 | 4336 | 36.1 |
| 60 | 120 | 120-150 | 86.3 | 4893 | 40.8 |

The freshly etched single layer pSi substrates were characterised using IRS, where a bifurcated optical fibre delivered tungsten light along the surface normal and collected reflected light into a CCD spectrometer. IRS was used to collect reflectance spectra of single layer pSi substrate etched at different current densities.[46] By means of a simulation program (SCOUT, obtained from M. Theiss Hard- and Software), which is based on the transfer matrix method, the best fit between the experimental and theoretical reflectance spectrum was used to determine porosity and thickness value of single layer pSi substrates.[65] The pSiRM substrate used in the optical biosensors was then designed via the SCOUT program based on the obtained porosity and thickness values of the single layer pSi substrate. The contrast of porosity and thickness was chosen to obtain an appropriate refractive-index profile of the pSiRM substrate with the position of the resonance cavity dip at the desired wavelength. The required current densities and etching time were also obtained via this method. The pSiRM substrates were fabricated by anodically etching a Si wafer using a current density alternating between 50 mA/cm$^2$ for 2288 ms and 25 mA/cm$^2$ for 1820 ms corresponding to HP and LP layers, respectively. The defect layer was etched at a current density of 50 mA/cm$^2$ for 9152 ms. The resulting pSiRM had the configuration (HP/LP)$_3$(HP)$_4$(LP/HIP)$_3$. The pSiRM substrate was also characterised using IRS to ensure that the reflectance spectrum matched that of the simulation. The single layer pSi and pSiRM substrates were analysed using SEM. A Quanta 450 field emission gun (FEG) Environmental SEM fitted with a Solid-State Detector (SSD) and an accelerating voltage of 30 kV was used.

Example 2

Peptide Functionalisation of pSiRM Substrates

A schematic representation of surface functionalisation reactions of a hydride-terminated pSiRM surface is shown in FIG. 1.

Freshly etched pSiRM substrates from Example 1 were functionalised by thermal hydrosilylation of neat undecylenic acid in a glass reaction flask. Before performing the reaction, the undecylenic acid was purged with argon for 15 min to remove any oxygen. The pSiRM substrates were then immersed in the undecylenic acid and purged for an additional 30 min. Afterwards, the reaction flask was immersed in an oil bath at 120° C. and the reaction proceeded for 3 h under an argon flow. Afterwards, the hydrosilylated pSiRM substrates were removed from the flask, rinsed with ethanol and dried gently under a stream of nitrogen gas. The hydrosilylated pSiRM substrates with a carboxylic acid-terminated surface was activated to form an NHS ester-terminated surface by reacting the pSiRM substrates with N-hydroxysuccinimide (NHS) (5 mM) in water in the presence of 1-(3-dimethylaminopropyl)-3-ethylcarbodiimide (EDC, Fluka) (5 mM) for 20min at room temperature. The substrates were then rinsed with water and dried gently under a stream of nitrogen gas. Immobilisation of the fluorogenic MMP peptide substrate [Dabcyl-Gaba-Pro-Gln-Gly-Leu-G1u(EDANS)-Ala-Lys-NH$_2$] (SEQ ID NO: 2), (Merck) was carried out by overnight incubation of the functionalised pSiRM surface with peptide (10 mM) in a buffer solution prepared from Trizma®Base (50 mM, pH 7.6), sodium chloride (NaCl, Chem Supply) (150 mM), calcium chloride dehydrate (CaCl$_2$.2H$_2$O, Ajax Chemical Ltd.) (5 mM), zinc chloride (ZnCl$_2$, Merck) (1 µM) and 0.01% Brij®L23.[11, 19] Afterwards, the surface was rinsed with water, 2:1 water/ethanol, 1:2 water/ethanol and ethanol. Finally, the pSiRM surface was dried gently under a stream of nitrogen gas. This modified pSiRM surface was then ready for use in biosensing.

FTIR analysis was conducted after each step of the surface functionalisation procedure. FTIR spectra were obtained using a Vertex 70 Hyperion microscope (Bruker) in the ATR mode. Background spectra were taken in air and sample spectra recorded over the range 650-4000 cm$^{-1}$, at a resolution of 22 cm$^{-1}$, an aperture size of 3 mm and averaging 64 scans. The base line was corrected and normalised with OPUS 7.2 Spectroscopy Software (Bruker). All samples for FTIR analysis were prepared from p-type Si wafer with a resistivity of 0.00055-0.001 Ωcm etched at current density 56 mA/cm$^2$ for 2 min.

Discussion

The freshly etched pSiRM substrate features a hydride-terminated surface. This surface is unstable and tends to oxidise in the presence of oxygen or to hydrolyse in the presence of water leading to uncontrollable optical properties which is undesirable for biosensor applications.[29, 31, 49] We functionalised the pSiRM surface by means of hydrosilylation of undecylenic acid. This produces a dense alkyl monolayer with stable Si—C bonds protecting the pSiRM surface from oxidative hydrolysis.[49, 50] The carboxylic acid can then be converted into a succinimidyl ester which reacts readily with the amine group of the fluorogenic MMP peptide substrate, as shown in FIG. 1(a).

The pSiRM substrates were characterised by Fourier Transform Infrared (FTIR) spectroscopy in the attenuated total reflectance (ATR) mode after every surface functionalization step (FIG. 1(b)). Hydrosilylation of the freshly etched pSiRM surface using neat undecylenic acid (Spectrum (i)) replaced the Si—H bonds on the surface with Si—C bonds. This was confirmed by the appearance of characteristic bands at 1459 cm$^{-1}$, 2865 cm$^{-1}$ and 2935 cm$^{-1}$ which were assigned to the $\delta_{CHtet}$ deformation mode of methylenes and the stretching vibrational of aliphatic C—H bonds, respectively. The characteristic band of $v_{C=O}$ stretching mode of a carboxylic acid was observed at 1714 cm$^{-1}$. The presence of very faint bands at 904 cm$^{-1}$ and 2100 cm$^{-1}$, assigned to Si—H$_2$ scissor vibrational mode and Si—H$_x$ stretching vibrational mode of the freshly etched pSi, respectively, indicate that there is a small amount of unreacted silicon hydride groups left on the surface. In addition, the band at 1033 cm$^{-1}$ attributed to the Si—O stretching vibrational indicates the presence of silicon dioxide at the surface of the pSiRM substrate. Residual silicon hydrides and a small amount of surface oxidation are commonly observed in the hydrosilylation of pSi.[49-52]

The activation of a grafted acid-terminated layer with EDC in the presence of NHS (Spectrum (ii)) resulted in further spectral changes including a triplet band at 1735 cm$^{-1}$, 1785 cm$^{-1}$ and 1815 cm$^{-1}$ which is characteristic for the formation of the NHS ester group.[49-51] The bands at 1735 cm$^{-1}$ and 1785 cm$^{-1}$ were assigned to the $v_{as(C=O)}$ antisymmetric stretching vibrational mode and to the $v_{s(C=O)}$ symmetric stretching vibration of the succinimidyl cycle, respectively, while the band at 1815 cm$^{-1}$ was assigned to two distinct chemical species, the $v_{s(C=O)}$ symmetric stretching vibrational mode and the $v_{(C=O)}$, stretching vibrational mode of the succinimidyl ester carbonyl.[49, 51] After immobilisation of the fluorogenic substrate, bands at 1660 cm$^{-1}$ and 1554 cm$^{-1}$ (Spectrum (iii)) appeared that were attributed to the amide I and amide ii bonds. The presence of those bands showed that the peptide was covalently bound to the pSiRM surface via amide bonds.[49]

These surface reactions were also followed using IRS to study the effects on the optical properties of the pSiRM substrate and in particular on the wavelength shift of the microcavity dip.[25] A red shift of 5 nm was observed after the hydrosilylation reaction, followed by a red shift after activation with succinimidyl ester ($\Delta\lambda=1$ nm) and then another red shift after immobilisation of the fluorogenic substrate ($\Delta\lambda=1$ nm). A small blue shift ($\Delta\lambda=0.5$ nm) was observed after incubation with MMP-1. Thus, overall the surface modification gave a total 6.5 nm red shift. These shifts needed to be considered when designing the wavelength position of resonance dip of the pSiRM substrate.

The 5 nm red shift after hydrosilylation can be explained by an increase in effective refractive index due to the monolayer formation of undecylenic acid within the porous layer. For example, Ouyang et al. observed the shift of microcavity dip after binding of thin layer molecules with different thickness considering some parameters, such as pore diameter and the refractive index changes before and after binding. They reported that a 10 nm red shift of the resonance cavity dip in the macroporous microcavity was produced by a 3 nm thick coating, which means, in our case, that for a 5 rim red shift, the monolayer thickness should be 1.5 nm.[25] This thickness is in reasonable agreement with what Böcking et al. observed for an undecylenic acid monolayer using X-ray reflectometry (0.9-1.1 nm).[53]

Example 3

Use as an Optical Biosensor

Prior to use in the biosensor experiments, Recombinant human MMP-1 (R&D Systems) was activated using previously published procedure.[11, 12] Freshly prepared 4-aminophenylmercuric acid (APMA, Aldrich) (100 mM) in dimethyl sulfoxide (Sigma-Aldrich) was added to recombinant human MMP-1 to give a final APMA concentration of 1 mM followed by the incubation at 37° C. for 3 h. The peptide functionalised pSiRM substrates were incubated in activated MMP-1 at varying concentrations at 37° C. for a few min and then rinsed with water, 2:1 water/ethanol, 1:2 water/ethanol and ethanol to remove unbound analytes. Afterwards, the substrates were dried gently under a stream of nitrogen gas. The dried pSiRM surface was placed in a cuvette with a special holder to support the pSiRM substrate. The cuvette was then placed in a fluorometer with the position of pSiRM surface facing the light source at a 36° angle. Finally, the fluorescence intensity of the fluorophore (EDANS) was measured using a fluorometer (Parkin Elmer LS 55 Luminescence Spectrometer). The emission was measured over a wavelength range of 360-540 nm at a fixed excitation wavelength of 340 nm, excitation and emission slit widths of 5 nm each, and a scan speed of 200 nm/min. The angle formed by the light source of the fluorometer and the defect layer of the pSiRM substrate in respect to the surface normal was set to 360 since we obtained highest fluorescence signals at this angle. Human wound fluid sample was collected from Women's and Children's Hospital (Adelaide, South Australia). The study protocol, which conformed to the ethical guidelines of the 1975 Declaration of Helsinki, was approved by the Health Service Human Research Ethics Committee and Central Northern Adelaide Health Service Ethics of Human Research Committee. The wound fluid was diluted 10-fold in buffer solution. The sensing platform was incubated in the wound fluid sample at 37° C. and then treated in the same ways as described above.

Results and Discussion

The optical biosensor investigated in this study was based on a photonic pSiRM substrate which consisted of two DBR and one resonance cavity layer. Each DBR had a periodic layer structure alternating between different porosities (HP and LP) with a quarter-wavelength ($\lambda/4$) optical thickness while the defect layer had a HP layer with an optical thickness of a multiple of half-wavelength ($\lambda/2$). The first task was to design a pSiRM substrate with appropriate porosity contrast between HP and LP layers. We therefore prepared five single layer pSi substrates etched at different current densities for 120 s. The samples were characterised morphologically and optically to determine pore size, porosity and thickness (see Table 1).

Figure 2:
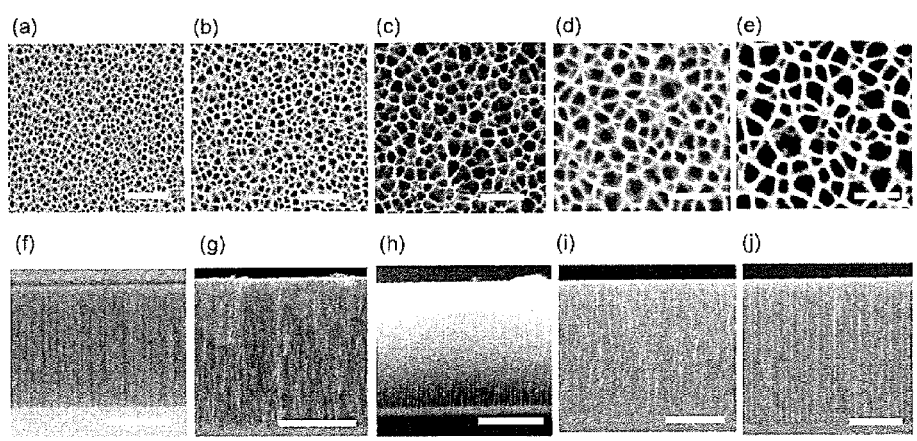
FIG. 2 shows: top view (a-e) and cross-sectional (f-j) SEM images of the single layer pSi etched at five different current densities as listed at Table 1. (a) and (f) are for current density 25 mA/cm$^2$, (b) and (g) are for current density 30 mA/cm$^2$, (c) and (h) are for current density 40 mA/cm$^2$, (d) and (i) are for current density 50 mA/cm$^2$, (e) and (j) are for current density 60 mA/cm$^2$. The scale bars presented in figure (a-e) and (f-j) are 300 nm and 2 m, respectively.

The average pore diameters and thickness were measured by means of scanning electron microscopy (SEM) (FIG. 2). The porosity and the thickness values were determined using interferometric reflectance spectroscopy (IRS) and a simulation using the transfer matrix method. The thickness values obtained from the simulation were in good agreement with the SEM result. The fringe patterns obtained for the single layer pSi samples are a result of Fabry-Pérot interferences and obey the equation:[24, 46, 47]

$$m\lambda = 2 \ nL \qquad (1)$$

where m is the fringe order, $\lambda$ is the wavelength of the incident light for maximum constructive interferences, n is the refractive index of the porous film, L is the film thickness and the factor of 2 is derived from the factor of 90° backscatter configuration of the light source and detector.[46, 48] The optical thickness of the film, the product of refractive index and film thickness can be determined from the reflectance spectrum by applying a fast Fourier transform (FFT).[48] The transfer matrix method was used to obtain the best fit between the experimental and the theoretical reflectance spectra over the spectrometer's wavelength range by adjusting the porosity and thickness parameters. Table SI shows that the pore diameter, porosity and thickness increased as the etching current density increased, as expected. The etching rate was calculated by dividing the thickness over the etching time.

Since we targeted MMPs and in particular MMP-1 which has a molecular weight of 42 kDa and unit cell dimensions of approximately of 14×14×11 nm$^3$,[44] a mesoporous pSiRM with pores >30 nm was required to allow MMP-1 ingress throughout the structure. This was achieved for all five etching conditions in Table 1. Once porosity, etching rate and pore size were determined for each current density profile, the pSiRM substrate could be designed and simulated using the transfer matrix method.[46] The mesoporous pSiRM substrate used in this study was designed with a symmetric mirror and a configuration of (HP/LP)$_3$(HP)$_4$(LP/HP)$_3$. Each DBR featured three periodic bilayers with a porosity of 83.4% for HP and a porosity of 67.0% for LP starting with HP for the first DBR and LP for the second DBR. Those porosity values produce pore diameters ranging from 40-60 nm for LP layer and 110-140 nm for HP layer, respectively. Those pore sizes were large enough to allow ingress of the desired target molecules while retaining the sensitivity of the biosensor. The pore size is an important parameter because it affects the internal surface area of the pSiRM substrate where the biorecognition molecules are attached and the target bioanalyte is captured.[25, 36] By decreasing the pore size, the internal surface area and the density of available binding sites for target bioanalytes are increased, which translates into higher sensitivity.[40] On the other hand, too small pore sizes prevent infiltration of large biomolecules into the entire porous layers.[25, 36] The chosen parameters therefore represent a compromise between these two requirements.

We observed that the surface modification of the pSiRM substrate influenced the position of the microcavity dip, requiring an adjustment of the etching conditions to compensate for those effects and achieve good alignment between the resonance cavity dip and the maximum fluorescence emission peak of the chosen fluorophore (in this case with EDANS at 446.5 nm). The good alignment between them leads to the enhancement effects of fluorescence emission of the fluorophore in the pSiRM substrate which is important for sensitive detection of MMPs as studied in this paper. The surface modification steps shifted the resonance cavity dip 6.5 nm towards longer wavelength (red shift). In order to compensate for the shift due to surface modification and produce the resonance cavity dip at 446.5 nm after surface modification, in this study, the pSiRM substrate was designed with a center wavelength ($\lambda$) of the resonance cavity dip at 440 nm measured at a light incidence angle of 36° or at 478 nm at 00 (a 38 nm blue shift from the angle of 0° to 360). However, the experimental result obtained by IRS also showed that the pSiRM substrate designed at 440 nm produced the resonance cavity dip at 448 nm (at an angle of 36°) corresponding to an 8 nm red shift different between design and the IRS experiment (FIG. 3($a$)). Therefore, to compensate for this shift and indeed produce the resonance cavity dip at 440 nm after etching or 446.5 nm after surface modification, as required for maximum overlap with EDANS emission, the pSiRM substrate was re-designed at 432 nm. In this design, the refractive indices (n) were 1.3 and 1.8 for the HP and LP layer, respectively, calculated using Bruggeman effective medium approximation. The value of n and $\lambda$ were used to determine the thickness of each periodic layer considering the $\lambda$/4 for each DBR and $\lambda$/2 for the defect layer. During the fabrication of the pSiRM substrate, the HP layer formed an 83 nm thick layer, while the LP layer formed a 60 nm thickness. It should be noted that the thickness values obtained from the simulation were in good agreement with the values obtained from SEM cross-sections of the produced pSiRM substrate.

Figure 3:
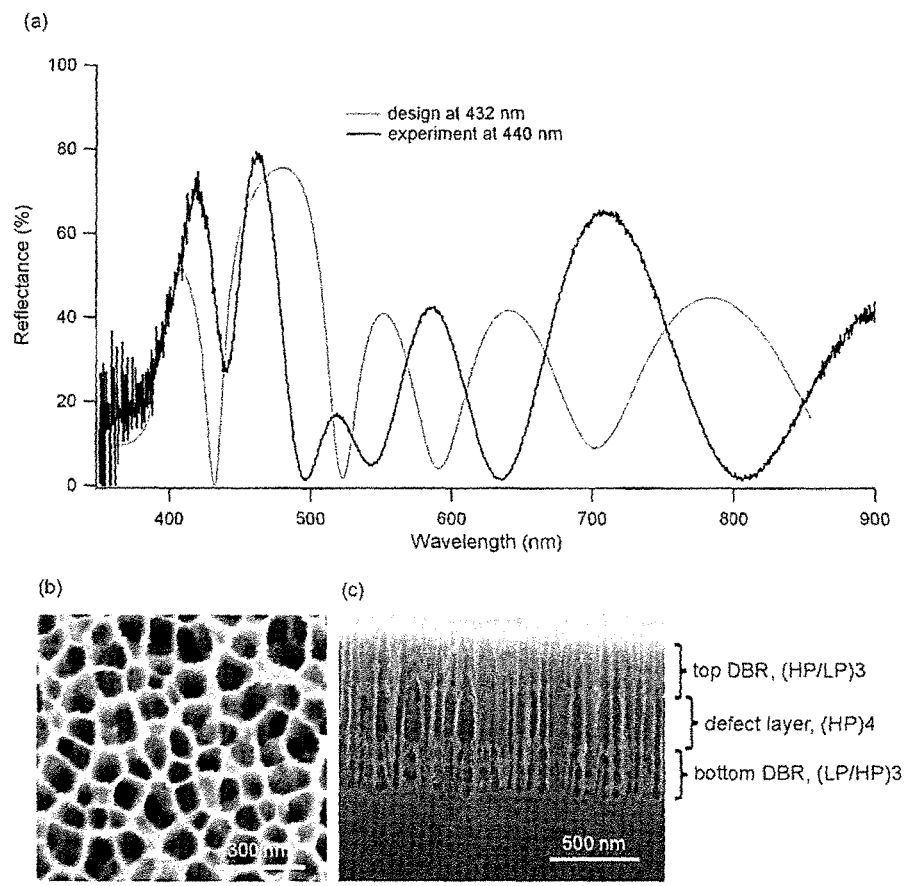
FIG. 3 shows: (a) a simulated reflectance spectrum of pSiRM (grey trace) and reflectance spectrum obtained using IRS from a freshly etched pSiRM (black trace); and (b) top view and (c) cross-sectional SEM images of a freshly etched pSiRM.

The surface was also characterised by SEM (FIG. 3($b$-$c$)) to obtain the top-view and cross-section images of the pSiRM substrate. FIG. 3($b$) shows the top view SEM image of mesoporous pSiRM substrate with the pore sizes ranged from 110-140 nm representing the pore size of the top layer of the DBR or in this case is the lip layer. The cross-sectional SEM image in FIG. 3($c$) reveals the periodic layers forming the pSiRM substrate, with the top and bottom DBR each featuring 3 periodic layers of HP/LP separated by an HP resonance cavity layer. The thickness of the periodic layer of the pSiRM substrate was 1.19 µm.

The peptide-functionalised pSiRM substrate was then used to detect MMP-1 in buffer solution. MMP-1 was chosen since this MMP is prominent in wound fluids.[54, 55] and is known to cleave the fluorogenic peptide sequence.[19] The sensing was performed by incubating the peptide-functionalised pSiRM substrate in the MMP-1 then rinsed and dried for measurement. A small blue shift ($\Delta\lambda$=0.5 nm) observed by IRS after incubation with MMP-1 on the pSiRM substrate gave a first indication that the peptide was indeed cleaved in the presence of MMPs. However, this small shift would limit the sensitivity of the device if the sensing was only done by IRS. Thus, we focused on an alternative approach to detect the MMP-1, exploiting fluorescence enhancement effects in the pSiRM structure.

Figure 4:
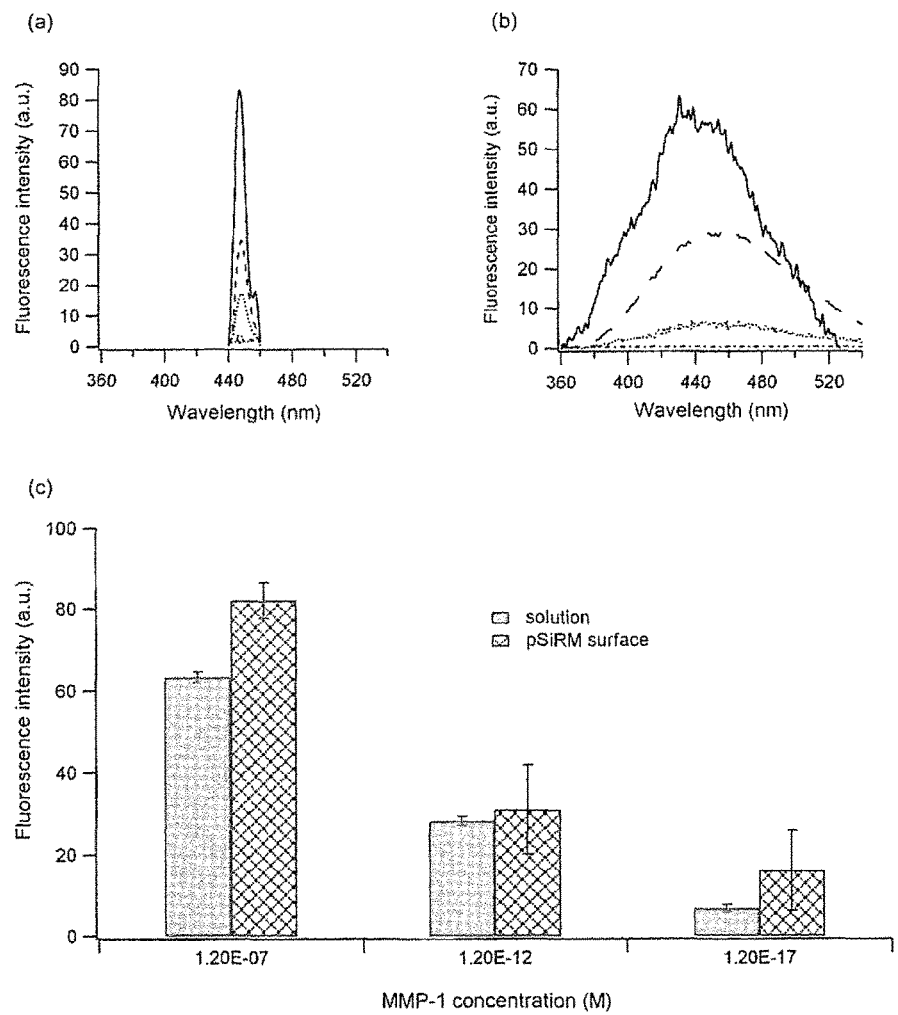
FIG. 4 shows EDANS emission spectra immobilised (a) in the pSiRM matrix; (b) in buffer solution from 3 different MMP-1 concentrations: $1.2\times10^{-7}$ M (full line); $1.2\times10^{-12}$ M (dashed line); $1.2\times10^{-17}$ M (dotted line) and 0 M (dot and dashed line); and (c) a plot of emission intensity at 446.5 nm for each concentration of MMP-1 in the buffer solution (solid) and on the pSiRM surface (pattern), with the error bars calculated from three separate experiments.

The peptide-functionalised pSiRM substrate in the absence of MMP-1 did not show any fluorescence at 446.5 nm, demonstrating that the Dabcyl moiety effectively quenched the EDANS fluorescence in the intact peptide (FIG. 4($a$)). However, when the pSiRM substrate was incubated with an MMP-1 containing solution for a few minutes, emission at 446.5 nm was observed, indicating that MMP-1 had indeed cleaved the peptide and removed the quencher. This result demonstrates that the immobilisation of the fluorogenic MMP peptide substrate into the pSiRM matrix did not prevent digestion by MMP-1. The fluorescence spectra generated from the pSiRM substrates after MMP-1 incubation were compared with the fluorescence signal of the fluorogenic substrates in the buffer solution at the same incubation time and MMP-1 concentration (FIG. 4($a$-$c$)). The comparison shows that the emission peak of the fluorophore in the solution (FWHM ~87 nm) was about ten times broader than the emission peak of the fluorophore attached on the pSiRM surface (FWHM ~8 nm). This conspicuous difference is testament to the effect of the pSiRM substrate in confining the width of the wavelength band that escapes the microcavity. In addition, the fluorescence intensity of the fluorophore embedded in the pSi matrix was higher than the fluorescence intensity of the fluorophore in the solution at the same MMP-1 concentration. We attribute this effect to the fluorescence enhancement of the microcavity.[37, 43, 56] The larger error bars for the pSiRM substrate compared to the solution measurement are probably due to slight variations in the surface concentration of the immobilised peptide for each sample.

Figure 5:
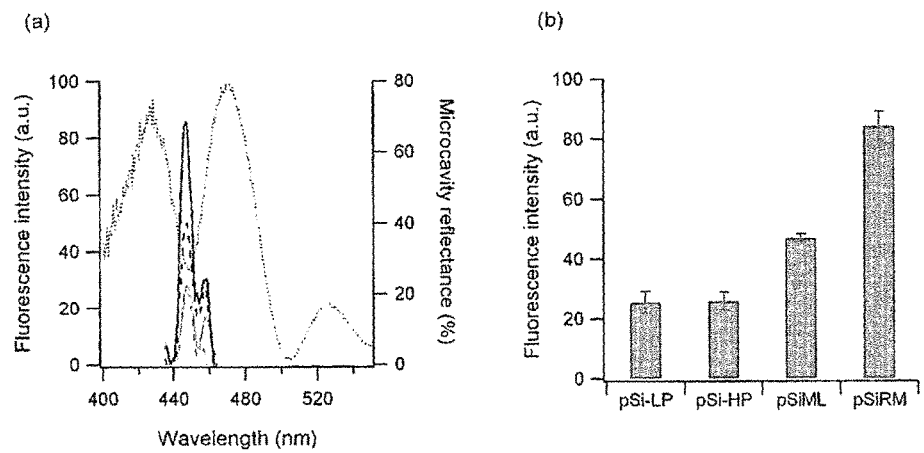
FIG. 5 shows fluorescence spectra of different pSi architectures (a): single layer pSi with low porosity (pSi-LP, grey dashed line), single layer pSi with high porosity (pSi-HIP, grey full line), multilayer pSi with alternating HP and LP layers (pSiML with resonance at 446.5 nm, black dashed line) and pSiRM (black full line). The dotted line represents the reflectance spectrum of pSiRM; and (b) a plot of emission intensities at 446.5 nm from four different pSi structures with the error bars calculated from three separate experiments.

Our results demonstrate that the emission from the pSiRM substrate is superior to emission in solution. We next investigated emission for different pSi architectures of identical thickness after incubation with MMP-1 ($1.2 \times 10^{-7}$ M) (FIG. 5). All samples had undergone the same surface modification procedure resulting in surfaces displaying fluorogenic peptide (as confirmed by IR spectroscopy).

FIG. 5($a$-$b$) shows that the EDANS emission intensity of the fluorophore embedded in the pSiRM substrate was about three times and two times higher compared to the single pSi layers (both HP and LP) and the pSi multilayer, respectively. This result confirms that the microcavity architecture is indeed able to enhance fluorescence emission[43] and that this platform may serve as a sensitive transducer for the presence of MMP-1 in solution.

Figure 6:
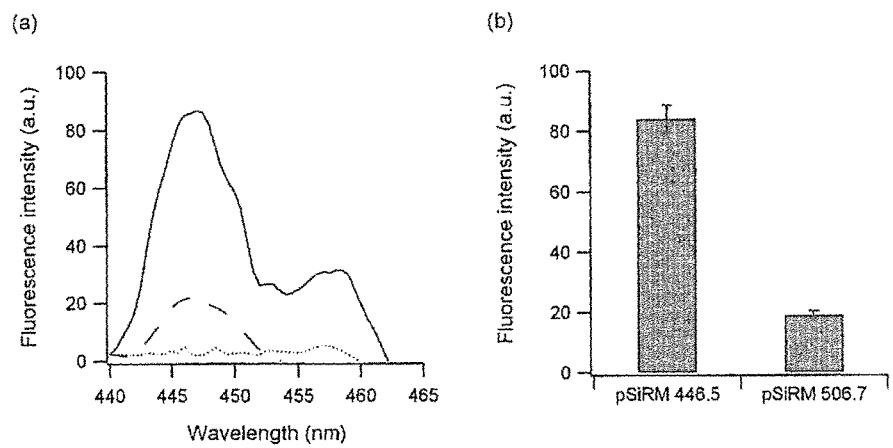
FIG. 6 shows: (a) comparison of fluorescence emission spectra observed at 446.5 nm from the pSiRMs with cavity dip at 446.5 nm (full line) and at 506.7 nm (dashed line) after incubation with MMP-1. The dotted line corresponds the control sample, which was not incubated with MMP-1; and (b) a plot of emission intensity at 446.5 nm of both pSiRM with the error bars calculated from three separate experiments.

We also investigated the effect of tuning the cavity to the emission wavelength of the fluorophore and compared two pSiRM substrates, one has a dip at 440 nm (designed at 432 nm) and the other at 500 nm (designed at 492 nm) after etching or before surface functionalisation (FIG. 6). The resonance of the freshly etched pSiRM substrate at 440 nm, was shifted into 446.5 nm after surface modification, as explained above, giving a perfect match with the emission maximum of EDANS. The other pSiRM substrate after surface modification gave a resonance peak at 506.7 nm, where EDANS embedded in the pSi layer does not have substantial emission.

FIG. 6 shows that after incubation with MMP-1 ($1.2 \times 10^{-7}$ M), the emission intensity of the tuned pSiRM substrate was about four times higher compared to the untuned one. This shows that optimal fluorescence is obtained when the wavelength of resonance cavity dip is tuned to the emission wavelength of fluorophore[43] and underscores that the resonance cavity layer is the sensitive part of the pSiRM substrate.

We then shifted our attention to the porosity contrast between LP and HP layer since this determines the Q factor, which is often a predictor of the sensitivity in an optical biosensor.[35, 36, 40] The Q factor is defined as $Q=\lambda/\Delta\lambda$, where $\lambda$ is the center wavelength of the resonance cavity dip and $\Delta\lambda$ is the full width at half maximum (FWHM) of the resonance cavity dip,[36, 39, 40] and indicates the effectiveness with which light is confined in the resonance cavity layer.[39] The Q factor can be increased by increasing the porosity contrast between LP and HP layers and also the number of periods in each DBR.

For the chosen configuration of $(HP/LP)_3(IP)_4(LP/HP)_3$, the porosity contrast was 16.4% and the reflectance spectrum (black trace in FIG. 1 (a)) gave a Q factor of 25 (measured at incident light 0°). There is no standard value of Q factor to produce a sensitive biosensor based on a pSiRM substrate.[57] DeLouise et al. reported that the pSiRM substrate with 20% porosity contrast had a Q factor of 28 for 5 periodic layer in the DBR and this value increased to 130 by doubling the number of periodic layer.[40] Palestino et al. showed that the pSiRM substrate with 15% porosity contrast and the Q factor of 40-50 was sensitive enough to detect 1-2 nm shift of the resonance peak.[37] The Q factor of our pSiRM substrate was slightly lower than that reported by DeLouise et al.

Figure 7:
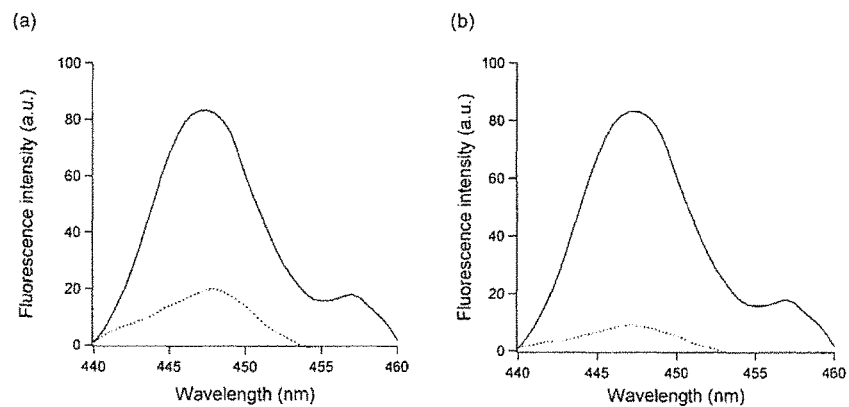
FIG. 7 shows plots of EDANS emission from (a) the pSiRM with (HP/LP)$_3$(HP)$_4$(LP/HIP)$_3$ and a 16.4% porosity contrast (full line) compared to a pSiRM with (HP/LP)$_3$(HP)$_4$(LP/HP)$_3$ and 19.3% porosity contrast (dotted line) and (b) the pSiRM with (HP/LP)$_3$(HP)$_4$(LP/HP)$_3$ and a 16.4% (full line) compared to a pSiRM with (HP/LP)$_4$(HP)$_4$(LP/HIP)$_4$ and 16.4% porosity contrast. The concentration of MMP-1 added to the surface was $1.2\times10^{-7}$ M.
Figure 8:
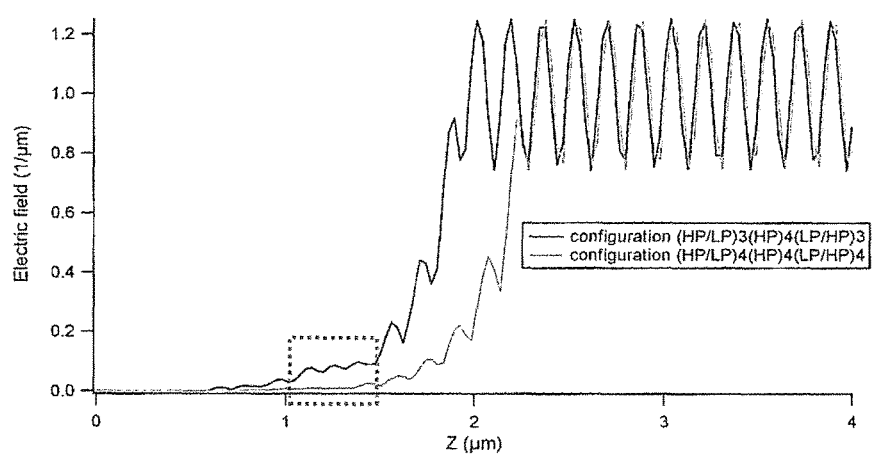
FIG. 8 is a plot showing the simulation of electric field distribution at excitation wavelength of EDANS (340 nm) throughout the porous layers of the same pSiRMs. The horizontal axis represents the position of the layer stack of the pSiRM structure which is specified as the spatial range for the electric field (z) starting from z=0.6 m at the pSi-bulk Si interface to z=1.8 μm as the pSi-air interface. The black trace represents the pSiRM with a configuration of (HIP/LP)$_3$(IP)$_4$(LP/HP)$_3$ and the grey trace represents the pSiRM with a configuration of (HP/LP)$_4$(HIP)$_4$(LP/HP)$_4$. The grey square shows the position of the defect layer in the layer stack of the pSiRM structure.

In order to investigate the influence of the Q factor value on biosensor performance, we increased the porosity contrast and the number of periods in each DBR. Note that for a pSiRM substrate with the same configuration of $(HP/LP)_3(HP)_4(LP/HP)_3$ but with a porosity contrast of 19.3% (86.3% for HP and 67% for LP) the Q factor increased to 44 (measured at incident light angle of 0°) and for a pSiRM substrate with the same porosity contrast but having four periodic layers in each DBR ($(HP/LP)_4(HP)_4(LP/HP)_4$), the Q factor was 45 (again measured at incident light angle of 0°). We compared these three pSiRM substrates and observed that the pSiRM substrate with a Q factor of 25 showed the highest EDANS emission intensity, producing a 4-fold and 8-fold higher signal than the pSiRM substrates with Q factors of 44 and 45, respectively, at the same concentration of MMP-1 ($1.2 \times 10^{-7}$ M) (FIG. 7). This finding shows that raising the Q factor by increasing the porosity contrast or the number of DBR periods did not translate into higher sensitivity in the biosensor (FIG. 7(b)). We attribute this interesting phenomenon to two effects: MMP infiltration and light distribution throughout the pSiRM layers. With higher porosity contrast, the difference in pore size between LP and HP also increases, resulting in potential trapping of MMP in the LP layer. This may negatively impact on the ability of MMP to cleave the peptide within the defect layer of the pSiRM substrate. For the thicker DBRs, the attenuation of excitation light at 340 nm becomes a problem since less light reaches the defect layer, reducing confined fluorescence emission. This effect is demonstrated in the simulation in FIG. 8, where the electric field distribution of the thinner cavity (black trace) in the defect layer is higher than for the thicker cavity (grey trace).

In POC diagnostic devices, a short response time and a low detection limit are highly desirable. Therefore, both parameters were investigated. We first studied the effect of incubation time with $1.2 \times 10^{-7}$ M MMP-1 on fluorescence signal level using the peptide-functionalised pSiRM substrate with the tuned cavity wavelength.

Figure 9:
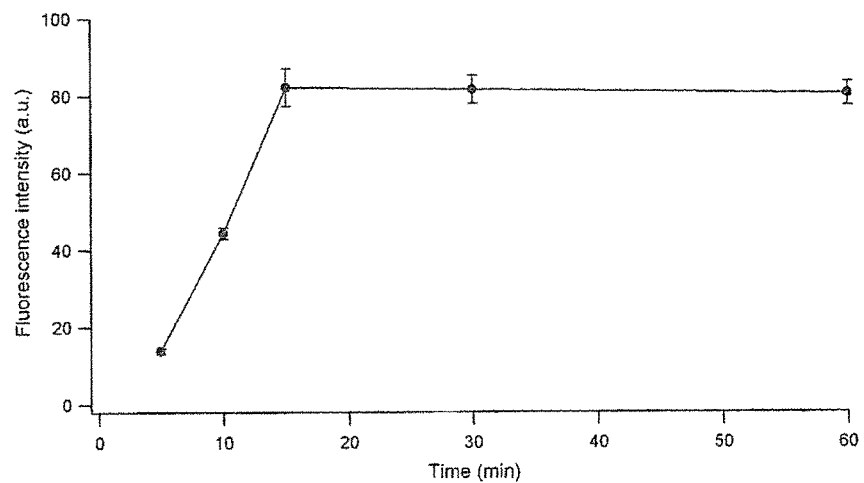
FIG. 9 shows a plot of fluorescence emission intensities for different incubation times. The error bars were calculated from three separate experiments.

FIG. 9 presents the EDANS fluorescence intensity at different incubation times. After 5 min of incubation, a significant fluorescence emission indicating the presence of MMP-1 was already detectable. The fluorescence intensity increased with increasing incubation time (due to increasing amounts of peptide cleavage) and then plateaued at 15 min incubation time (when apparently all fluorogenic peptide was cleaved). Therefore, 5 min of incubation time and a single incubation and washing step sufficed to generate a strong optical signal in response to MMP-1 solution, which is encouraging for a POC biosensor.

Figure 10:
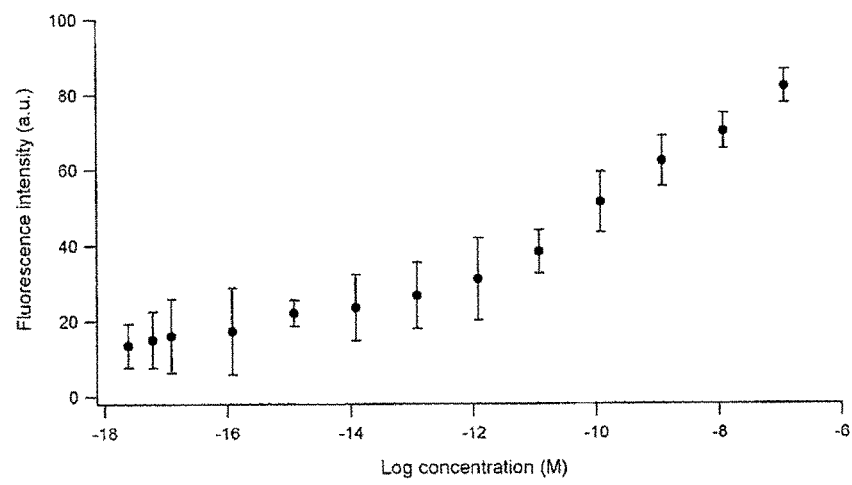
FIG. 10 shows a plot of fluorescence emission intensity of peptide-functionalised pSiRM after incubation with MMP-1 at different concentrations for 15 min. The error bars were calculated from the three separate experiments.

The fluorescence emission intensity after incubation with different concentrations of MMP-1 (logarithmic scale) is shown in FIG. 10. The optical signal increased linearly with increasing MMP-1 concentration from $10^{-7}$ M to $10^{-12}$ M (five orders of magnitude) with a linear regression equation of $y=10.345x+153.37$ ($R^2=0.99535$). At lower concentrations, the fluorescence intensity increased only gradually with increasing MMP-1 concentration. This effect was attributed to the diffusion of the small amount MMP-1 inside the cavity layer generated a pre-concentration effect.[43] The lowest concentration of MMP-1 we attempted to detect was $2.4 \times 10^{-18}$ M. However, to determine the limit of detection (LOD), we use the equation of $$LOD = y_b + 3Std_b \qquad (2)$$

where $y_b$ is the concentration of blank (control solution in the absence of MMP-1) and $Std_b$ is the standard deviation of blank. From this equation, the calculated LOD was $7.5 \times 10^{-19}$ M.

To the best of our knowledge, this represents by far the most sensitive MMP biosensor for MMPs detection. Gogly et al. reported a detection limit as low as $2.4 \times 10^{-15}$ M in the case of an MMP-1 assay on collagen zymograms.[58, 59] Using surface plasmon resonance (SPR) Jung et al., were able to detect MMP-3 in the range of $9.3 \times 10^{-10}$ M-$3.7 \times 10^{-7}$ M.[60] A single-walled carbon nanotube based assay had a detection limit of $7.4 \times 10^{-12}$ M for MMP-3.[61] The MMPs biosensor based on the pSiRM structure developed by Martin et al. which observing the shift of the cavity during sensing was able to detect as low as $1.5 \times 10^{-9}$ M MMP-8.[21]

Figure 11:
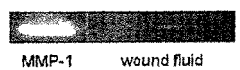
FIG. 11 shows a Western Blotting analysis for wound fluid sample and MMP-1 as a positive control.

The peptide-functionalised pSiRM biosensor detected MMP-1, as representative of MMPs, in buffer solution with excellent sensitivity. Following this, the same sensing platform was applied to detect MMPs in wound fluid, which contains a large number of biomolecules that could potentially interfere with the biosensor.[45, 62-64] The wound fluid sample used in this study was the aliquot of the wound fluid sample used in our previous study. It was human chronic wound fluid collected from six subjects with chronic venous leg ulcers attending the multidisciplinary foot clinic at The Queen Elizabeth Hospital (South Australia, Australia).[23] Western Blot of this wound fluid (FIG. 11) confirmed the presence of MMPs.[23]

Figure 12:
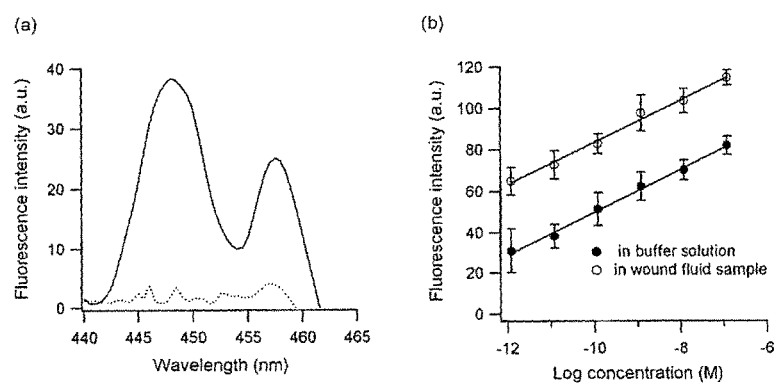
FIG. 12 shows: (a) a plot of fluorescence emission spectra of peptide-functionalised pSiRM after immersion in wound fluid (WF) (full line). The dotted line corresponds to the control pSiRM not incubated with wound fluid; and (b) a plot of average emission intensity of different concentration of MMP-1 in buffer solution and spiked to wound fluid sample with error bars calculated from three separate experiments.
Figure 13:
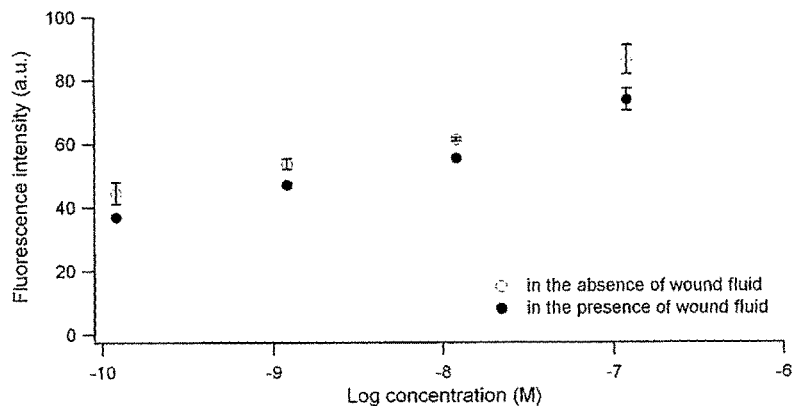
FIG. 13 shows a plot of the fluorescence emission intensity of neat dye in the presence and absence of wound fluid at four different concentrations with error bars calculated from three separate experiments.

Upon incubation of the peptide-functionalised pSiRM with a tuned cavity dip in wound fluid we observed a strong emission signal after 15 min, confirming the presence of MMPs in the wound fluid (FIG. 12(a)). In order to determine potential matrix effects in wound fluid, the fluorescence intensity of the wound fluid sample spiked with the different concentration of MMP-1 (1.2×10-7 M, 1.2×10-8 M, 1.2× 10-9 M, 1.2×10-10 M, 1.2×10-11 M and 1.2×10-12 M) was determined. The signal generated from wound fluid sample containing MMP-1 produced a linear response with the linear regression equation of y=10.188x+185.52 (R2=0.99115). Both calibration curves (FIG. 12(b)), in buffer solution (taken from a linear range of FIG. 10) and in wound fluid, gave a similar slope, demonstrating the absence of matrix effects. Using the standard addition approach, the signal from wound fluid in FIG. 8(a) corresponds to 1.5× 10-15 M. In order to study the possible impact of a large number of biomolecules including protein in the wound fluid sample on the fluorescence signal, the fluorescence emission of the various concentrations of neat dye in the presence and absence of the wound fluid were compared (FIG. 13). The results showed that the presence of protein and other biomolecules in wound fluid sample only slightly decreased the fluorescence signals. Our results confirm that the emission signal of the pSiRM after incubation with wound fluid was due to the MMP-catalyzed cleavage of the immobilised fluorogenic peptide substrate and that the presence of other molecules in the wound fluid did not cause significant interferences.

Example 4

Detection of Wound Biomarkers

In this example, MMP was detected in real biological samples, including wound fluid samples and a tissue extract sample using the method described in Example 3. The samples were obtained from the patients attending wound clinic, but the identity and also the type of wound were concealed, thus the samples were labelled based on the label on the sample vials as received.

Figure 14:
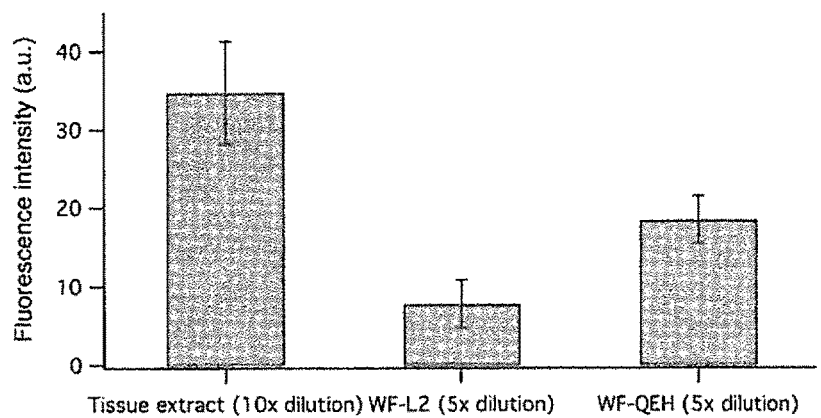
FIG. 14 shows a plot of the fluorescence emission intensity of peptide-functionalised pSiRM after incubation with tissue extract (left) and two different sources of wound fluid (middle and right)

The fluorescence intensity of the EDANS after cleavage by the MMP in the wound sample is shown in FIG. 14. The plot shows that the biosensor of the present invention was able to detect MMP in wound fluid samples and also in other biological samples, in this case, tissue extract.

Example 5

Selectivity of Biosensor Toward MMPs

The MMP specific fluorogenic peptide substrate immobilised on the pSiRM substrate is not selectively cleaved by any one type of MMP. Indeed, the fluorogenic peptide substrate can be cleaved by MMP-1, -2, -3 and -9 with different catalytic activity.[69] As a consequence, during sensing in complex biological media such as wound fluid or other body fluids, the specific MMP detected by the pSiRM sensing platform cannot be identified.

We have improved the selectivity of the pSiRM biosensor by employing magnetic nanoparticles (MNPs). The MNPs are functionalised with MMP antibody (MMPAb) to harvest the MMP from buffer solution or from wound fluid samples. The MNPs can be modified with any type of MMPAb depending on the targeted MMP. For example, the MNPs are immobilised with MMP-1Ab in order to target MMP-1. The MNP-MMP-1Ab binding MMP-1 (MNP-MMP-1Ab-MMP-1) is then incubated with pSiRM functionalised with the fluorogenic peptide substrate. The fluorescence signal after cleaving, observed fluorimetrically, can be used to confirm the presence of MMP-1 without any interference from other MMPs. Therefore, the biosensor can be used for the selective detection of a specific peptide or protein in a family of structurally related peptides or proteins.

The MNPs used for this experiment have a particle size of 10 nm with carboxylic acid terminated groups enabling immobilisation of an MMP antibody via amide coupling. The particle size of MNP is small enough to facilitate an easy infiltration of nanoparticles throughout the porous layer of pSiRM. The surface chemistry used to immobilise the MMPAb on the MNP surface is similar to that used to immobilise MMP fluorogenic peptide substrate on the pSiRM surface.

Figure 15:
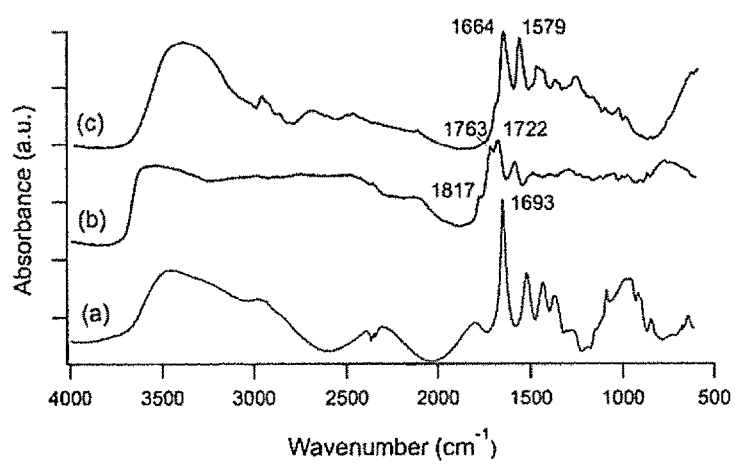
FIG. 15 shows FTIR spectra of MNP surface functionalization. (a) Carboxylic acid terminated MNPs, (b) carboxylic acid terminated MNPs after activation using EDC/NHIS and (c) immobilization of MMP-1Ab on MNPs.

The MNPs were prepared as follows. MNPs with terminal carboxylic acid groups were washed and then activated using EDC/NHS to form the NHS ester, which was then further reacted with amine groups of the MMP antibody. This reaction was confirmed using Fourier transform infrared spectroscopy (FTIR), as shown in FIG. 15. The FTIR results show that the MNP containing carboxylic acid groups displays a peak at 1693 cm$^{-1}$ which is characteristic of the C—O carboxylic group. After activation with EDC/NHS, the characteristic triplet peak of C═O from the NHS ester group appeared at 1722, 1763 and 1817 cm$^{-1}$. The covalent immobilisation of MMP-1Ab was confirmed with the presence of the bands at 1664 and 1579 cm$^{-1}$ which correspond to the amide I and II bonds.

The MNPs immobilised with 500 gig/mL MMP-1Ab (MNP-MMP-1Ab) were then interacted with 1.2×10$^{-12}$ M MMP-1 at 37° C. for 5 min. The functionalised nanoparticle (MNP-MMP-1Ab-MMP-1) was then separated from the MMP-1 solution using a magnetic column and diluted in 100 µL buffer solution. This 100 µL buffer solution containing MNP-MMP-1Ab-MMP-1 was then incubated in the solution containing MMP fluorogenic MMP peptide substrate for 15 min and then the fluorescence intensity of EDANS after cleavage was measured (FIG. 16(a)). The sensing test was also conducted in the pSiRM sensing platform (pSiRM functionalised with fluorogenic MMP peptide substrate) for 15 min and then the fluorescence intensity was measured (FIG. 16(b)).

Figure 16:
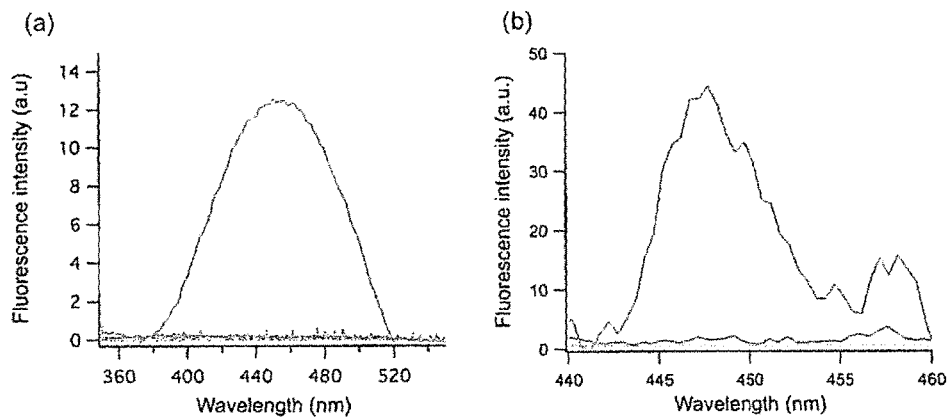
FIG. 16 shows fluorescence emission spectra of the EDANS from MMP fluorogenic peptide substrate detected in the solution (a) and the pSi surface after incubated with MMP-1 immobilised in MNP-MMP-1Ab.

The result presented in FIG. 16 shows that fluorescence observed in the solution (upper trace FIG. 16(a)) and pSiRM sensing platform (upper trace FIG. 16(b)) indicates the MMP-1 bound in MNP-MMP-1Ab was still active and able to cleave the peptide substrate. It confirmed that the binding of MMP-1 to MMP-1Ab has no effect on the MMP-1 activity. The fluorescence intensity was also higher compared to the fluorescence intensity of the MMP-1 detection reported before (without MNP). This result confirmed that the utilisation of MNP increasing the ability to capture the MMP and effectively cleaving the MMP peptide substrate immobilised on the pSiRM sensing platform. As a control experiment, the MNP-MMP-1Ab, without MMP-1, was also incubated with pSiRM sensing platform. After 15 min incubation, there was no fluorescence signal detected (lower trace in FIG. 16(a) and 16(b)). This shows that the fluorescence signal is due to the presence of MMP-1 cleaving the MMP substrate and the MNP or MMP-1Ab did not affect the fluorescence signal.

Figure 17:
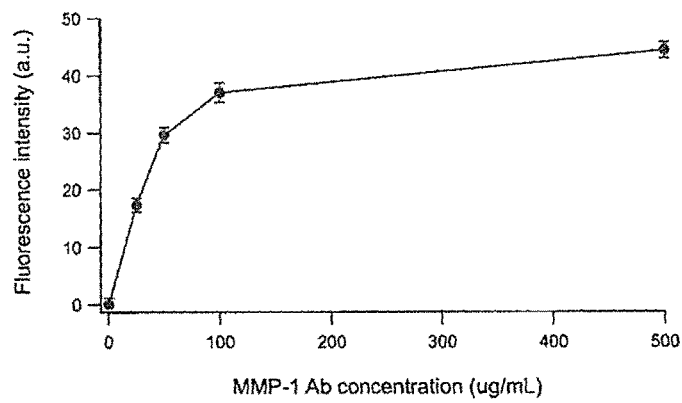
FIG. 17 shows a plot of fluorescence intensity of the EDANS from the MMP fluorogenic peptide substrate after cleavage by MMP-1 bound with MNP-MMP-1Ab at different concentration of MMP-1Ab.

The concentration of MMP-1Ab immobilised on the MNP was then optimised. Five different concentrations were tested; 0, 25, 50, 100 and 500 µg/mL (FIG. 17). The graph in FIG. 17 shows that the concentration of MMP-1Ab affects the fluorescence intensity confirms that the higher the concentration of MMP-1Ab, the more MMP-1 captured and, therefore, the more MMP fluorogenic peptide substrate cleaved.

Figure 18:
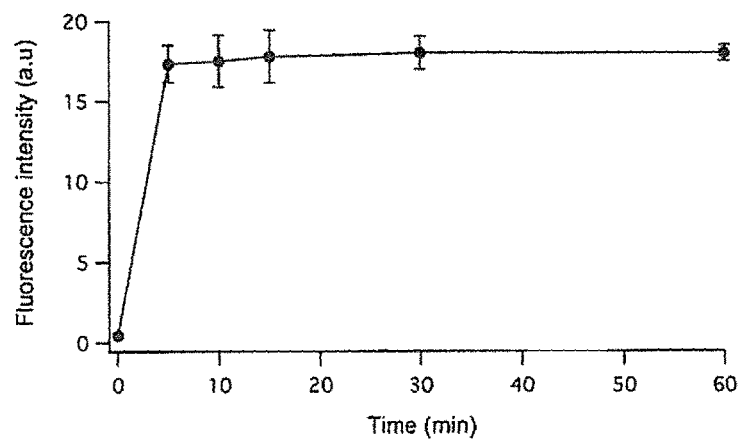
FIG. 18 shows a plot of fluorescence intensity of the EDANS from the MMP fluorogenic peptide substrate after cleavage by MMP-1 bound with MNP-MMP-1Ab at different interaction time between MMP-1Ab and MMP-1.

After optimising the concentration of MNP-1Ab, we optimised the interaction time between MNP-MMP-1Ab (25 µg/mL of MMP-1Ab) with MMP-1 ($1.2 \times 10^{-12}$ M). The concentration of MMP-1Ab used was 25 µg/mL as the lowest concentration tested in the previous experiment but this already provided an obvious signal. Six different time was tested; 0, 5, 10, 15, 30 and 60 min, as shown in FIG. 18. From the figure, it can be seen that within 5 min most of MMP-1 was captured by MMP-1Ab and there was no significant difference when the time was increased. This shows that the utilisation of MNP-MMP-1Ab is an effective and fast method to harvest MMP in buffer solution.

Figure 19:
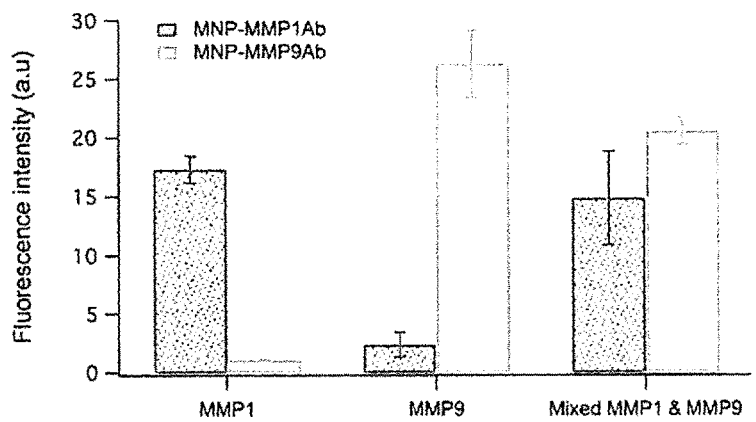
FIG. 19 shows a plot showing the selectivity of MNP-MMPAb in buffer solution containing MMP-1, MMP-9 and mixed MMP-1 MMP-9.
Figure 20:
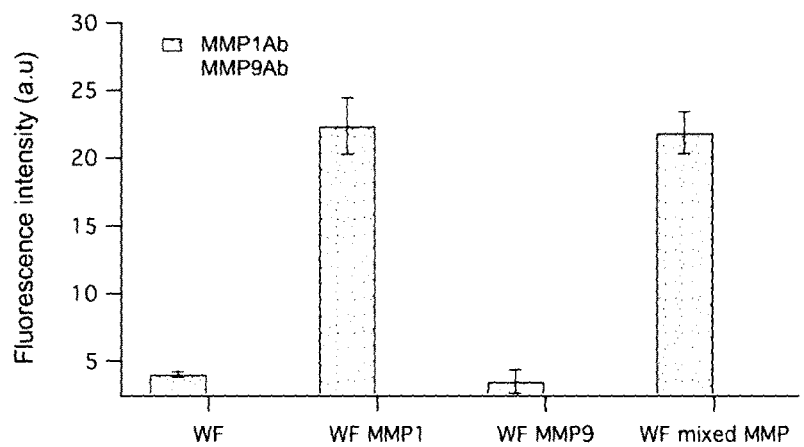
FIG. 20 shows a plot showing the selectivity test of MNP-MMPAb in wound fluid sample, wound fluid spiked with MMP-1, MMP-9 and mixed MMP-1 MMP-9.

After optimising the interaction time and antibody concentration, we then tested the selectivity of this system in buffer (FIG. 19) and wound fluid (FIG. 20). In order to do that, we prepared two functionalised MNPs. One was MNP functionalised with MMP-1Ab (MNP-MMP-1Ab) and the other one was MNP functionalised with MMP-9Ab (MNP-MMP9Ab). Each of the MNP functionalised antibody was then interacted for 5 min with $1.2 \times 10^{-12}$ M of MMP-1 in buffer, $1.2 \times 10^{-12}$ M of MMP-9 in buffer and mixed MMP-1 ($1.2 \times 10^{-12}$ M) and MMP-9 ($1.2 \times 10^{-12}$ M) in buffer. The MNP functionalised antibody which already bind MMP, was then incubated in pSiRM sensing platform for 15 min and then the fluorescence was measured.

The first two bar charts in FIG. 19 show the fluorescence intensity of the EDANS after cleavage by MMP-1 captured by MNP-MMP-1Ab (left bar (dotted)) and MNP-MMP9Ab (right bar). These charts show that the fluorescence intensity was higher in the sample incubated with MNP-MMP-1Ab binding MMP-1 (about 17.3±1.1) than the sample incubated with MNP-MMP9Ab binding MMP-1 (about 1.0±0.1). The small amount of MMP-1 detected in MNP-MMP9Ab may due to the small amount of MMP-1 trapped in the MNP during the washing steps after MNP-MMP9Ab interacted with MMP-1 solution thus interfere the measurement.

In the second two bar charts, a similar trend is shown. The fluorescence intensity of EDANS cleaved by MMP-9 bound with MNP-MMP9Ab (right bar) is higher (25.5±2.8) compared to MMP-9 bound with MNP-MMP-1Ab (left bar (dotted)) (2.3±1.1) confirming that MNP-MMP9Ab has higher affinity to MMP-9.

In the third two bar charts, when MMP-1 and MMP-9 were mixed together in buffer solution, the fluorescence intensity of EDANS after interaction with MNP-MMP-1Ab (left bar (dotted)) and MNP-MMP9Ab (right bar) is 14.9±4.0 and 20.5±1.1, respectively. This value is about the same as the fluorescence intensity of the EDANS when MNP-MMPAb was contacted with the buffer solution containing only one MMP. It demonstrates that in the mixture of MMP, the MNP-MMPAb selectively bind the MMP.

The selectivity test was also conducted in a wound fluid sample (FIG. 20). The MNP functionalised MMPAb (MNP-MMP-1Ab and MNP-MMP9Ab) was added to a wound fluid sample, in separate vials for each MMPAb, to harvest the MMP-1 and MMP-9. The MNP-MMPAb-MMP was then incubated with the functionalised pSiRM for 15 min before fluorescence intensity was observed by means of a fluorimeter.

As seen in the first two bar chart in FIG. 6, the fluorescence intensity of EDANS emitted from the surface incubated with MNP-MMP9Ab (7.7±0.8) is higher than the intensity of the EDANS emitted from the surface incubated with MNP-MMP-1Ab (4.1±0.2) indicating the wound fluid sample contains more MMP-9 than MMP-1. The MNP-MMP-1Ab and MNP-MMP9Ab were also contacted with wound fluid sample spiked with $1.2 \times 10^{-12}$ M of MMP-1, $1.2 \times 10^{-12}$ M of MMP-9 and mixed MMP-1 MMP-9 with each concentration of $1.2 \times 10^{-12}$ M (WF MMP-1, WF MMP9 and WF mixed MMP in FIG. 20, respectively).

From FIG. 20, it can be seen that in wound fluid sample spiked with MMP-1 (WF MMP-1), the fluorescence intensity of EDANS observed in the functionalised pSi surface after incubation with MNP-MMP-1Ab (left bar, 22.4±2.1) was higher compared to the surface incubated with MNP-MMP9Ab (right bar, 6.5±0.6). The value of the fluorescence intensities were contributed to by the MMP-1 present in wound fluid and MMP-1 spiked in the wound fluid sample and if they are reduced from the fluorescence signal observed only in the wound fluid sample (signal in the first two bar charts), the fluorescence intensity was similar to the fluorescence signal observed after MNP-MMPAb binding the MMP-1 in buffer solution (the first two bar charts in FIG. 19).

A similar trend was also observed when MNP-MMP9Ab interacted with wound fluid spiked with MMP-9. The fluorescence intensity observed on the surface incubated with MNP-MMP9Ab was higher (28.6±1.0) than the surface incubated with MNP-MMP-1Ab (3.5±0.9). If this value is reduced from the fluorescence intensity of unspiked wound fluid sample, the fluorescence signal is in agreement with the fluorescence signal detected in buffer solution (FIG. 19).

In the wound fluid sampled spiked with mixed MMP, the fluorescence signal detected on the pSiRM functionalised surface after incubation with MNP-MMP-1Ab and MNP-MMP9Ab was 21.9±1.6 and 28.9±1.1, respectively. These intensity values were also in agreement with the fluorescence intensity of mixed MMP in buffer solution if they were reduced from their fluorescence intensity in the wound fluid sample. This confirmed that selective binding using MNP-MMPAb can be employed in complex biological samples.

Example 6

MMP Detection by Means of a Confocal Microscope

Figure 21:
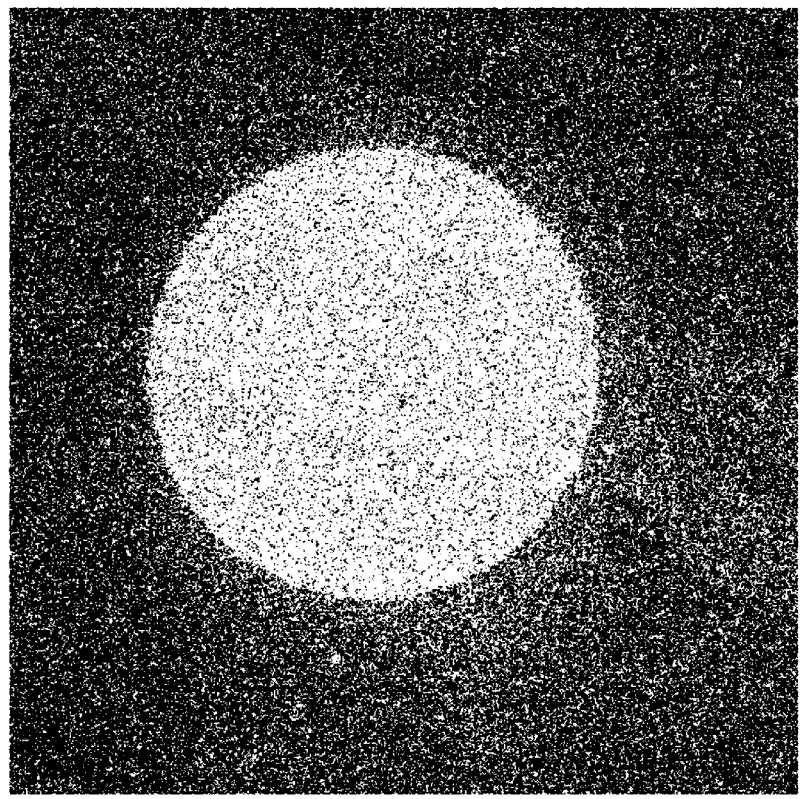
FIG. 21 shows a confocal microscope image of a pSiRM surface functionalised using a microcontact printing technique to immobilise the MMP peptide substrate and then incubated with MMP-1 solution.

Besides using a fluorimeter, the fluorescence detection of EDANS emissions after cleavage by MMP were investigated using a confocal microscope. The pSiRM surface was functionalised using a microcontact printing technique to immobilise the MMP peptide substrate. The functionalised surface was then incubated with MMP-1 solution and viewed under microscope (FIG. 21). The lighter circle is the surface where the MMP peptide substrate was immobilised while the darker surrounding surface is the area where there was no immobilised peptide. The lighter colour (blue) is the colour of EDANS emission confirming the cleavage of the MMP substrate. This result confirms that it is also possible to detect the fluorescence emission under microscope.

Example 7

Detection of the Bacterial Biomarker Sortase A

The biosensor described can also be used to detect other analytes for example bacterial enzymes, such as the bacterial Sortase A enzyme. This enzyme is used by Gram-positive bacteria *Staphylococcus aureus* to anchor surface protein to the cell wall by cleaving LPXTG at the amide bond between threonine and glycine. The LPXTG is a general tag where X is any amino acid, however LPETG (where X is E) is the optimal isoform of the tag.[72]

We designed a detection agent specific for Sortase A. The substrate sequence was Dnp-LPETG-(K-FITC)-NH$_2$, where 2,4-dinitrophenol (Dnp) is the fluorescence acceptor, FITC (Fluorescein isothiocyanate) is the fluorescence donor and T-G (Threonine-Glycine) as the linker. This substrate was synthesised commercially.

Since the Sortase A substrate has amine groups similar to MMP substrate, the immobilisation of the Sortase A substrate was conducted in a similar way to the MMP peptide substrate, as described in Example 2. However, the pSiRM as sensing platform was re-designed to have a microcavity dip aligned with FITC emission of the FRET substrate after cleavage, which is about 514 nm.

Initially, we tested the ability to detect Sortase A in solution and on the pSiRM surface. A solution of 1 mM Sortase A substrate was contacted with 1 µg/mL Sortase A for 30 min and then the FITC emission was measured by fluorimeter (FIG. 22(a)). The same concentration of Sortase A was immobilised on the pSiRM surface. The surface was then contacted with the same concentration of Sortase A for 30 min and FITC emission was measured (FIG. 22(b)).

Figure 22:
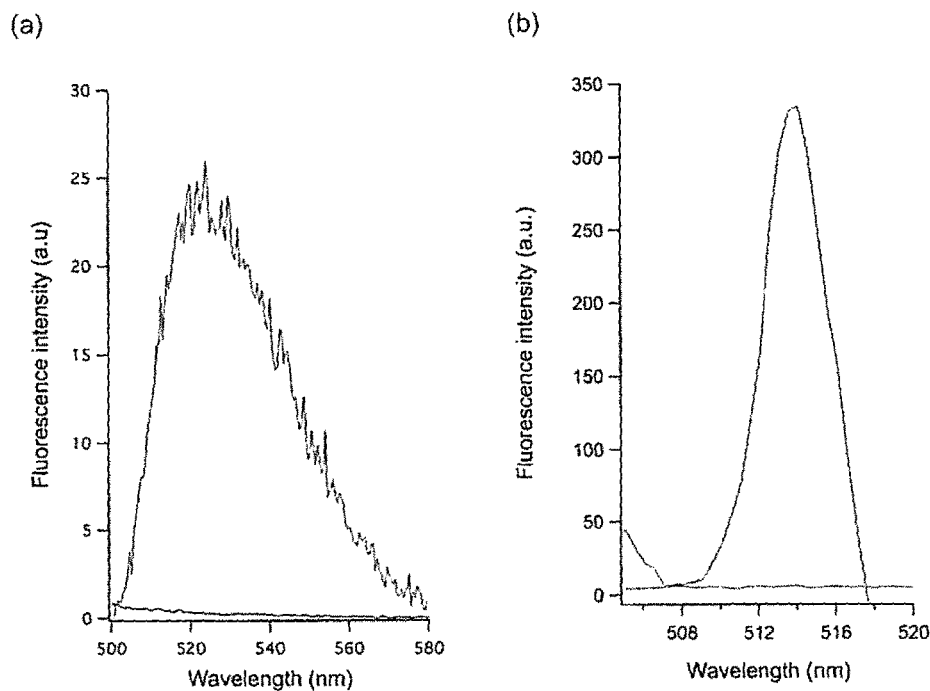
FIG. 22 shows the fluorescence emission (top trace) of FITC detected on solution (a) and pSiRM surface (b) after cleaved by Sortase A, while the lower trace is the blank which is the Sortase A substrate solution (a) and functionalised pSiRM surface (b) before contact with Sortase A enzyme.

FIG. 22 shows the emission of FITC after the Sortase A substrate cleaved by Sortase A enzyme and the fluorescence emission of the FITC is 4.3 times higher in pSiRM surface (FIG. 22(b)) compared to the emission detected in solution (FIG. 22(a)). It confirms the fluorescence enhancement effect of the pSiRM sensing platform.

Figure 23:
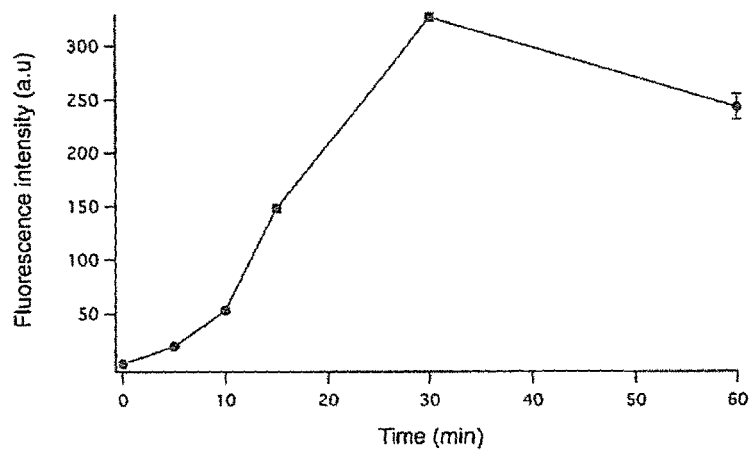
FIG. 23 shows the fluorescence intensity of the FITC from the Sortase A peptide substrate after cleavage by Sortase A at different contact times with the error bars calculated from three different experiments.

We then optimised the time required to cleave the Sortase A substrate. We contacted 1 µg/mL Sortase A with 1 mM Sortase A substrate immobilised on pSiRM surface for six different times; 0, 5, 10, 15, 30 and 60 min and then the fluorescence emission was measured as shown in FIG. 23. From this figure, it can be seen that the longer the interaction between Sortase A enzyme and Sortase A substrate the higher emission of the FITC detected, confirming more Sortase A is cleaved by the enzyme. However this trend was only until 30 min contact time. After that time, the fluorescence intensity observed decreased indicating the fluorescence emission of FITC may start to be quenched in that duration. In any event, the 5 min interaction time to obtain a fluorescence signal and 30 min to obtain maximum fluorescence signal is an ideal time for sensing.

Figure 24:
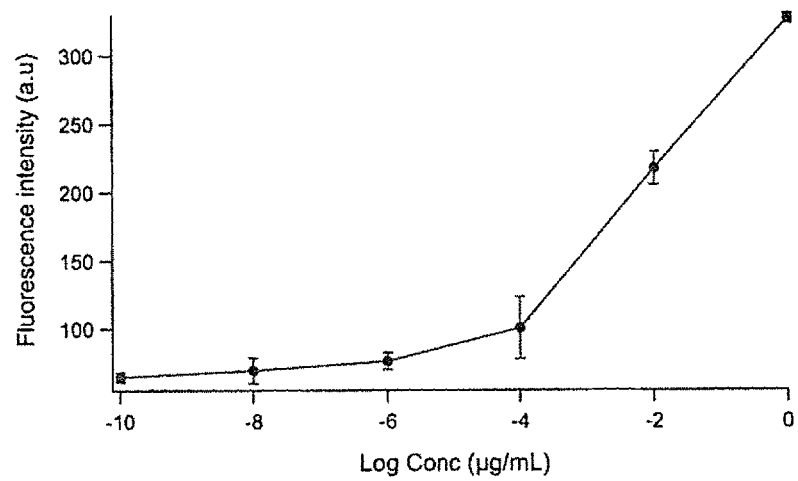
FIG. 24 shows the fluorescence intensity of the FITC from the Sortase A peptide substrate after cleavage by Sortase A at different concentrations of Sortase A enzyme with the error bars calculated from three separate experiments.

The next step was to optimise the concentration of Sortase A that can be detected. To do this, the concentration of the Sortase A substrate was kept constant at 1 mM and then we tested six different concentrations from 1 µg/mL down to $1\times10^{-10}$ µg/mL as shown in FIG. 24. The figure shows that the fluorescence signal decreased along with the lower concentration of Sortase A enzyme and this sensing platform still had an obvious signal down to fg/mL of Sortase A concentration.

Figure 25:
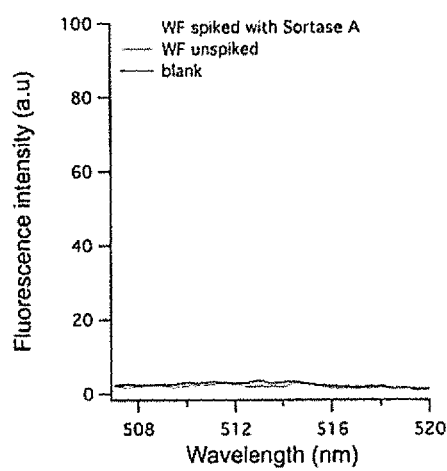
FIG. 25 shows the fluorescence intensity of the FITC from the Sortase A peptide substrate from a wound fluid experiment.

Sortase A was also detected in wound fluid (FIG. 25). The Sortase A substrate immobilised on pSiRM sensing platform was contacted with wound fluid sample (lower trace) and wound fluid spiked with $1\times10^{-4}$ µg/mL Sortase A (upper trace) for 30 min and then the fluorescence intensity of FITC was measured.

FIG. 25 shows that the wound fluid sample did not give any fluorescence signal (lower trace) indicating the wound fluid did not contain any Sortase A enzyme. Therefore, we tried to add the wound fluid sample with $1\times10^{-4}$ µg/mL Sortase A enzyme and measured the emission (upper trace). The wound fluid sample spiked with Sortase A emitted the FITC fluorescence with the intensity about 82.34 a.u., which is close to the emission of that concentration in buffer solution as presented in FIG. 24 (100.2±22.7 a.u.). This result indicates the enzyme was still active and able to cleave the Sortase A substrate even in a complex sample.

Figure 26:
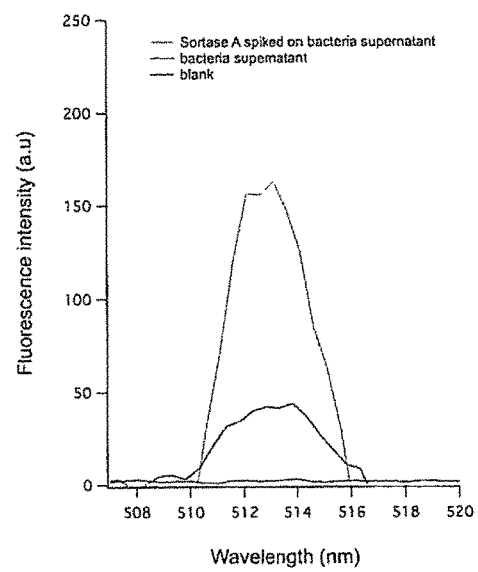
FIG. 26 shows the fluorescence intensity of the FITC from the Sortase A peptide substrate after cleaved by bacteria supernatant sample.

Since the wound fluid sample did not contain the enzyme, we conducted another experiment using a bacterial supernatant sample from *Staphylococcus aureus* bacteria. The bacteria supernatant was a bacteria culture media which was inoculated with *S. aureus* and then filtered. This filtered media or supernatant was then used for the experiment. Initially, we tried to inoculate the media with *S. aureus* for 1 h and check the fluorescence emission as presented in FIG. 26 (lower trace). From the figure, it can be seen that the bacterial supernatant sample gave a fluorescence emission signal (about 47.26 a.u.) indicating the Sortase A substrate was cleaved by the Sortase A enzyme presented in the bacterial supernatant sample. However, in order to confirm that signal, we also spiked the bacterial supernatant with $1\times10^{4}$ µg/mL of Sortase A enzyme (upper trace). Spiking the bacterial supernatant sample with Sortase A enzyme increased the fluorescence intensity about 112.19 a.u., which is in agreement with the emission in detected when pSiRM surface interacted with $1\times10^{-4}$ g/mL of Sortase A enzyme in solution (FIG. 24). These results demonstrate that the fluorescence emission signal detected in bacterial supernatant sample was due to the presence of Sortase A enzyme in that sample.

Figure 27:
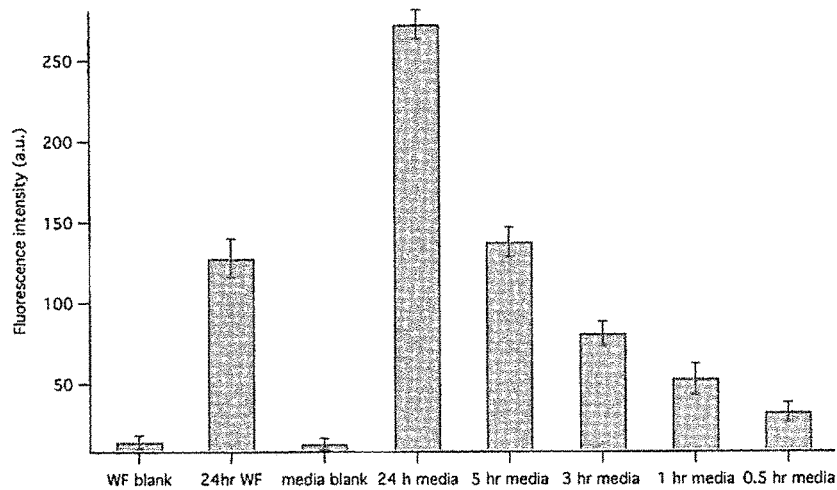
FIG. 27 shows the fluorescence intensity of the FITC from the Sortase A peptide substrate after cleavage by bacteria supernatant sample with different inoculation times (0, 0.5, 1, 3, 5 and 24 h) and wound fluid sample inoculated with bacteria for 0 and 24 h with the error bars calculated from three separate experiments.

This bacterial supernatant experiment was then followed with a bacterial supernatant experiment which was carried out with different inoculation times; 0, 0.5, 1, 3, 5 and 24 h and also inoculated wound fluid sample for 0 and 24 h, as presented in FIG. 27.

FIG. 27 shows that fluorescence emission generated from the surface incubated with bacterial supernatant from bacteria culture media increased along with the increasing inoculation time. It confirms the longer the inoculation time, the more Sortase A enzyme produced. In the supernatant sample from bacterial culture media and wound fluid sample at 0 h inoculation time had very small amount of Sortase A enzyme as indicated by the very low emission fluorescence detected. However, after 24 h inoculation time, the Sortase A enzyme produced in the inoculated bacterial culture sample was higher compared to the enzyme produced in the inoculated wound fluid sample indicating the faster Sortase A enzyme in bacterial culture media.

Figure 28:
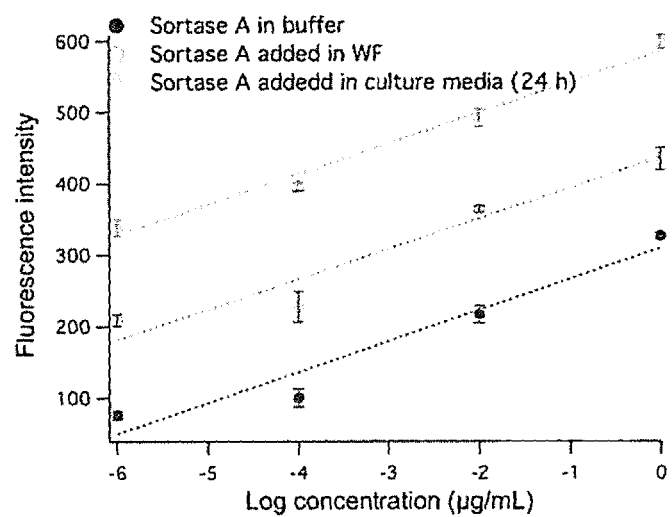
FIG. 28 shows a comparison of emission intensity of different concentration of Sortase A in buffer solution (full circle), added in wound fluid sample (open circle) and added in bacterial supernatant sample (triangle). The error bars were calculated from three separate experiments.

Finally to confirm that there was no matrix effect, we used a standard addition approach and compared the fluorescence signal of FITC after cleavage by Sortase A enzyme in buffer solution, spiked in wound fluid sample and spiked in bacterial supernatant sample (FIG. 28). In order to do that, we tested four different concentrations of Sortase A enzyme which gave a linear response as detected in previous experiment (FIG. 24). From the results in FIG. 28, it can be seen that all the samples gave a similar slope indicating no interference matrix effect.

CONCLUSION

We present a fluorescence-based optical biosensor for MMP-1 which was designed around a photonic pSiRM substrate that was carefully designed by considering parameters such as pore size, porosity, Q factor, number of periods in the DBRs, the angle of the incident light and the corresponding wavelength of the photonic band gap. The pSiRM surface was functionalised with a fluorogenic peptide substrate for MMP as confirmed by FTIR-ATR spectra.

The EDANS emission observed in the pSiRM surface was stronger and narrower than the emission observed in solution at the same MMP-1 concentration, due to confinement and enhancement effects in the pSiRM substrate, and also stronger compared to other pSi architectures such as single layer and multilayer. Tuning of the cavity position to the EDANS emission peak was found to be essential.

The presence of MMP-1 in buffer solution was detected after 5 min and a single incubation step. In addition, this biosensor successfully detected MMP-1 with a limit of detection of $7.5 \times 10^{-19}$ M. MMP detection was also achieved for human chronic wound fluid, which is the clinically relevant sample for this type of biosensor. Thus, our results set the stage for the development of much needed POC biosensors that underpin improvements in the management of chronic wounds.

It will be appreciated by those skilled in the art that the invention is not restricted in its use to the particular application described. Neither is the present invention restricted in its preferred embodiment with regard to the particular elements and/or features described or depicted herein. It will be appreciated that the invention is not limited to the embodiment or embodiments disclosed, but is capable of numerous rearrangements, modifications and substitutions without departing from the scope of the invention as set forth and defined by the following claims.

REFERENCES

[1] K. Harding, Principles of Best Practice: Diagnostics and Wounds. A concensus Document, London, 2007.

[2] T. R. Dargaville, B. L. Farrugia, J. A. Broadbent, S. Pace, Z. Upton, N. H. Voelcker, *Biosens. Bioelectron.* 2013, 41, 30.

[3] H. Brem, O. Stojadinovic, R. F. Diegelmann, H. Entero, B. Lee, I. Pastar, M. Golinko, H. Rosenberg, M. Tomic-Canic, *Mol. Med.* 2007, 13, 30.

[4] C. K. Sen, G. M. Gordillo, S. Roy, R. Kirsner, L. Lambert, T. K. Hunt, F. Gottrup, G. C. Gurtner, M. T. Longaker, *Wound Rep. Reg.* 2009, 17, 763.

[5] T. Velnar, T. Bailey, V. Smrkolj, *J. Int. Med. Res.* 2009, 37, 1528.

[6] N. Mehmood, A. Hariz, R. Fitridge, N. H. Voelcker, *J. Biomed. Mater. Res., Part B* 2013, 00B, 000.

[7] N. T. Thet, S. H. Hong, S. Marshall, M. Laabei, A. Toby, A. Jenkins, *Biosens. Bioelectron.* 2013, 41, 538.

[8] J. Zhou, A. L. Loftus, G. Mulley, A. T. A. Jenkins, *J. Am. Chem. Soc.* 2010, 132, 6566.

[9] J. Zhou, T. N. Tun, S.-h. Hong, J. D. Mercer-Chalmers, M. Laabei, A. E. R. Young, A. T. A. Jenkins, *Biosens. Bioelectron.* 2011, 30, 67.

[10] K. G. Harding, H. L. Morris, G. K. Patel, *BMJ* 2002, 324, 160.

[11] Y. Cao, T. I. Croll, S. C. Rizzi, G. K. Shooter, H. Edwards, K. Finlayson, Z. Upton, T. R. Dargaville, *J. Biomed. Mater. Res.* 2011, 96A, 663.

[12] W. Bode, C. Fernandez-Catalan, H. Tschesche, F. Grams, H. Nagase, K. Maskos, *Cell. Mol. Life Sci.* 1999, 55, 639.

[13] J. L. Gorman, E. Ispanovic, T. L. Haas, *Drug Discovery Today: Dis. Models* 2011, 8, 5.

[14] R. Visse, H. Nagase, *Circ. Res.* 2003, 92, 827.

[15] R. P. Verma, C. Hansch, *Bioorganic and Medicinal Chemistry* 2007, 15, 2223.

[16] N. J. Trengove, M. C. Stacey, S. Macauley, N. Bennett, J. Gibson, F. Burslem, G. Murphy, G. Schultz, *Wound Rep. Reg.* 1999, 7, 442.

[17] J. F. Woessner, *FASEB J.* 1991, 5, 2145.

[18] H. F. Bigg, A. D. Rowan, *Curr. Opin. Pharmacol.* 2001, 1, 314.

[19] B. Beekman, J. W. Drijfhout, W. Bloemhoff, H. K. Ronday, P. P. Tak, J. M. te Koppele, *FEBS Lett.* 1996, 390, 221.

[20] L. Gao, N. Mbonu, L. Cao, D. Gao, *Anal. Chem.* 2008, 80, 1468.

[21] M. Martin, C. T. Bendiab, L. Massif, G. Palestino, V. Agarwal, F. Cuisinier, C. Gergely, *Phys. Status Solidi C* 2010, 1.

[22] K. A. Kilian, L. M. H. Lai, A. Magenau, S. Cartland, K. Gaus, J. J. Gooding, *Nanoletters* 2009, 9, 2021.

[23] F. S. H. Krismastuti, A. J. Cowin, S. Pace, E. Melville, T. R. Dargaville, N. H. Voelcker, *Aust. J. Chem.* 2013.

[24] A. Jane, R. Dronov, A. Hodges, N. H. Voelcker, *Trends Biotechnol.* 2009, 27, 230.

[25] H. Ouyang, C. C. Striemer, P. M. Fauchet, *Appl. Phys. Lett.* 2006, 88, 1631081

[26] H. Ouyang, L. A. DeLouise, B. L. Miller, P. M. Fauchet, *Anal. Chem.* 2007, 79, 1502.

[27] E. J. Anglin, L. Cheng, W. R. Freeman, M. J. Sailor, *Adv. Drug Delivery Rev.* 2008, 60, 1266.

[28] S. P. Low, N. H. Voelcker, L. T. Canham, K. A. Williams, *Biomaterials* 2009, 30, 2873.

[29] M. Arroyo-Hernandez, R. J. Martin-Palma, J. Perez-Rigueiro, J. P. Garcia-Ruiz, J. L. Garcia-Fierro, J. M. Martinez-Duart, *Mater. Sci. Eng., C* 2003, 23, 697.

[30] B. Guan, A. Magenau, K. A. Kilian, S. Ciampi, K. Gaus, P. J. Reece, J. J. Gooding, *Faraday Discuss.* 2011, 149, 301.

[31] K. A. Kilian, T. Bocking, J. J. Gooding, *Chem. Commun.* 2009, 630.

[32] T. C. Do, H. Bui, T. V. Nguyen, T. A. Nguyen, *Adv. Nat. Sci.: Nanosci. Nanotechnol.* 2011, 2, 035001.

[33] S. Li, J. Huang, L. Cai, *Nanotechnology* 2011, 22, 425502 (6pp).

[34] L. De Stefano, I. Rendina, L. Moretti, S. Tundo, A. M. Rossi, *Applied Optics* 2004, 43.

[35] G. Palestino, V. Agarwal, D. B. Garcia, R. Legros, E. Perez, C. Gergely, *Optical Characterization of Porous Silicon Microcavities for Glucose Oxidase Biosensing, Vol. 6991* (Eds.: J. Popp, W. Drexler, V. V. Tuchin, D. L. Matthews), SPIE, 2008, pp. 69911 Y.

[36] H. Ouyang, M. Christophersen, R. Viard, B. L. Miller, P. M. Fauchet, *Adv. Funct. Mater.* 2005, 15, 1851.

[37] G. Palestino, V. Agarwal, R. Aulombard, E. Perez, C. Gergely, *Langmuir* 2008, 24, 13765.

[38] L. De Stefano, L. Rotiroti, E. De Tommasi, I. Rea, I. Rendina, M. Canciello, G. Maglio, R. Palumbo, *J. Appl. Phys.* 2009, 106, 0023109.

[39] L. A. DeLouise, P. M. Fauchet, B. L. Miller, A. A. Pentland, *Adv. Mater.* 2005, 17, 2199.

[40] L. A. DeLouise, P. M. Kou, B. L. Miller, *Anal. Chem.* 2005, 77, 3222.

[41] S. Chan, S. R. Horner, P. M. Fauchet, B. L. Miller, *J. Am. Chem. Soc.* 2001, 123, 11797.

[42] S. Chan, Y. Li, L. J. Rothberg, B. L. Miller, P. M. Fauchet, *Mater. Sci. Eng., C* 2001, 15, 277.

[43] B. Sciacca, F. Frascella, A. Venturello, P. Rivolo, E. Descrovi, F. Giorgis, F. Geobaldo, *Sens. Actuators, B* 2009, 137, 467.

[44] S. Iyer, R. Visse, H. Nagase, K. R. Archarya, *Jornal of Molecular Biology* 2006, 362, 78.

[45] D. Hanson, D. Langemo, P. Thompson, J. Anderson, S. Hunter, *Advances in Skin and Wound Care* 2005, 18, 360.

[46] S. Pace, R. B. Vasani, F. Cunin, N. H. Voelcker, *New J. Chem.* 2013, 37, 228.

[47] V. S.-Y. Lin, K. Motesharei, K. Dancil, M. J. Sailor, M. R. Ghadiri, *Science* 1997, 278, 840.

[48] C. Pacholski, M. Sartor, M. J. Sailor, F. Cunin, G. M. Miskelly, *J. Am. Chem. Soc.* 2005, 127, 11636.

[49] T. Bocking, K. A. Kilian, K. Gaus, J. J. Gooding, *Adv. Funct. Mater.* 2008, 18, 3827.

[50] R. Boukherroub, J. T. C. Wojtyk, D. D. M. Wayner, D. J. Lockwood, *J. Electrochem. Soc.* 2002, 149, 1159.

[51] S. Sam, L. Touahir, J. Salvador Andresa, P. Allongue, J. N. Chazalviel, A. C. Gouget-Laemmel, C. Henry de Villenueve, A. Moraillon, F. Ozanam, N. Gabouze, S. Djebbar, *Langmuir* 2009, 26, 809.

[52] B. Sciacca, E. Secret, S. Pace, P. Gonzalez, F. Geobaldo, F. Quignard, F. Cunin, *J. Mater. Chem.* 2011, 21, 2294.

[53] T. Bocking, E. L. S. Wong, M. James, J. A. Watson, C. L. Brown, T. C. Chilcott, K. D. Barrow, H. G. L. Coster, *Thin Solid Films* 2006, 515, 1857.

[54] B. A. Mast, G. S. Schultz, *Wound Rep. Reg.* 1996, 4, 411.

[55] U. K. Saarialho-Kere, *Arch. Dermatol. Res.* 1998, 290, S47.

[56] A. Venturello, C. Ricciardi, F. Giorgis, S. Strola, G. P. Salvador, E. Garrone, F. Geobaldo, *J. Non-Cryst. Solids* 2006, 352, 1230.

[57] H. Ouyang, P. M. Fauchet, Biosensing using Porous Silicon Photonic Bandgap Structures, 2005.

[58] B. Gogly, N. Groult, W. Hornebeck, G. Godeau, B. Pellat, *Anal. Biochem* 1997, 255, 211.

[59] C. Lombard, J. Saulnier, J. Wallach, *Biochemie* 2005, 87, 265.

[60] S.-H. Jung, D.-H. Kong, J. H. Park, S.-T. Lee, J. Hyun, Y.-M. Kim, K.-S. Ha, *Analyst* 2010, 135, 1050.

[61] B. S. Munge, J. Fisher, L. N. Millord, C. E. Krause, R. S. Dowd, J. F. Rusling, *Analyst* 2010, 135, 1345.

[62] S. A. Eming, M. Koch, A. Krieger, B. Brachvogel, S. Kreft, L. Bruckner-Tuderman, T. Krieg, J. D. Shannon, J. W. Fox, *J. Proteome Res.* 2010, 9, 4758.

[63] R. W. Tarnuzzer, G. S. Schultz, *Wound Rep. Reg.* 1996, 4, 321.

[64] D. R. Yager, B. C. Nwomeh, *Wound Rep. Reg.* 1999, 7, 433.

[65] M. Born, E. Wolf, Principles of Optics: Electromagnetic Theory of Propagation, Interference and Diffraction of Light, seventh ed., Cambridge University Press, New York, 1999.

[66] Boukherroub R. et al., "Passivated luminescent porous silicon," J. Electrochem. Soc. 148, (9), 1191-1197, 2001.

[67] Hurley P. T., Ribbe A. E., Buriak J. M., "Nanoscale alkyne electrografting on silicon," Am. Soc. J. Chem. 125, (37), 11334-11339, 2003.

[68] Lakowicz. J. R. Principles of Fluorescence Spectroscopy, 2nd ed., New York: Plenum Press, 1999.

[69] Beekman, B. et al. Convenient Fluorometric Assay for Matrix Metalloproteinase Activity and Its Application in Biological Media. *FEBS Lett.* 390, 221-225, 1996.

[70] Clapp, A. R. et al. Fluorescence Resonance Energy Transfer Between Quantum Dot Donors and Dye-Labeled Protein Acceptors, J. Am. Chem. Soc. 126, 301-310, 2004.

[71] Rundhaug, J. E. Matrix Metalloproteinases, Angiogenesis, and Cancer, Clin. Cancer Res. 9, 551, 2003.

[72] Parthasarathy, R., Subramanian, S. & Boder, E. T. Sortase A as a Novel Molecular "Stapler" for Sequence-Specific Protein Conjugation. *Bioconjugate Chemistry* 18, 469-476 2007.

Throughout the specification and the claims that follow, unless the context requires otherwise, the words "comprise" and "include" and variations such as "comprising" and "including" will be understood to imply the inclusion of a stated integer or group of integers, but not the exclusion of any other integer or group of integers.

The reference to any prior art in this specification is not, and should not be taken as, an acknowledgement of any form of suggestion that such prior art forms part of the common general knowledge.

The invention claimed is:

1. An optical biosensor for detecting a target bioanalyte in a sample, the biosensor comprising:
   a porous silicon or alumina substrate comprising a surface and a detection agent immobilised on the surface, the detection agent comprising a sensing domain and a signaling domain, the sensing domain comprising a linker capable of interacting with the target bioanalyte and the signaling domain comprising a luminescence donor and a luminescence acceptor wherein the luminescence donor and the luminescence acceptor are connected by the linker and are optically coupled in the absence of the target bioanalyte such that emission of light from the luminescence donor is substantially quenched by the luminescence acceptor, and interaction of the target bioanalyte with the linker results in optical un-coupling of the luminescence donor and the luminescence acceptor to thereby result in light emission from the luminescence donor; and
   a plurality of light interacting pores on the surface of the substrate, wherein the pores are configured to interact with the light emission from the luminescence donor to provide a measurable light emission which is indicative of the presence of the target bioanalyte.

2. The optical biosensor according to claim 1, further comprising a detector for detecting light emission from the luminescence donor and provide an output signal containing information on said light emission.

3. The optical biosensor according to claim 1, wherein the linker is cleavable by the target bioanalyte when it contacts the linker such that cleavage of the linker results in optical un-coupling of the luminescence donor and the luminescence acceptor.

4. The optical biosensor according to claim 1, wherein an internal surface of the light interacting pores comprises an optical structure that interacts with the light emission from the luminescence donor.

5. The optical biosensor according to claim 4, wherein the optical structure is an optical filter, reflector or cavity.

6. The optical biosensor according to claim 1, wherein the substrate is a resonant microcavity (pSiRM) substrate in which the light interacting pores comprise distributed Bragg reflectors separated by a resonant microcavity.

7. The optical biosensor according to claim 6, wherein the substrate shows a resonance microcavity dip in the centre of the reflectance band in a reflectance spectrum and the wavelength of the microcavity dip is substantially the same as the emission wavelength of the luminescence donor so that the emission from the luminescence donor is enhanced by the microcavity.

8. The optical biosensor according to claim 6, wherein the resonance microcavity dip of the pSiRM is sensitive to refractive index changes and a relatively small refractive index change induces a relatively large shift in the optical spectrum.

9. The optical biosensor according to claim 6, wherein each distributed Bragg reflector comprises a periodic layer structure alternating between high porosity silicon and low porosity silicon.

10. The optical biosensor according to claim 6, wherein the optical thickness of each distributed Bragg reflector is a quarter-wavelength and the optical thickness of the microcavity is half-wavelength and the wavelength is the emission wavelength of the fluorescence donor.

11. The optical biosensor according to claim 1, wherein the luminescence donor and the luminescence acceptor are a fluorescence donor/acceptor pair or a phosphorescence donor/acceptor pair.

12. The optical biosensor according to claim 11, wherein the luminescence donor and the luminescence acceptor are a fluorescence donor/acceptor pair.

13. The optical biosensor according to claim 1, wherein the target bioanalyte is a peptide or protein of interest.

14. The optical biosensor according to claim 1, further comprising a bioanalyte specific capture agent deposited on or near the surface of porous silicon or porous alumina substrate of the biosensor.

15. The optical biosensor according to claim 14, wherein the bioanalyte specific capture agent is in the form of particles comprising binding agent on the surface thereof.

16. The optical biosensor according to claim 15, wherein the binding agent binds the target bioanalyte selectively from complex fluids comprising other components that are structurally related to the target bioanalyte.

17. A detection device comprising the optical biosensor according to claim 1, comprising a fluid inlet through which a sample can be introduced, a housing for the optical biosensor, and an optical output to output information on the emission intensity of the fluorescence donor.

18. A method for detecting a target bioanalyte in a sample, the method comprising:
   providing an optical biosensor according to claim 1;
   contacting the surface of the optical biosensor with the sample to allow interaction of the target bioanalyte (if present) and the linker;
   detecting a change in light emission from the optical biosensor; and
   using the detected change in light emission to provide an indication of the presence of the target bioanalyte.

19. A method for measuring the concentration of a target bioanalyte in a sample, the method comprising:
   providing an optical biosensor according to claim 1;
   contacting the surface of the optical biosensor with the sample to allow interaction of the target bioanalyte (if present) and the linker;
   detecting a change in light emission from the optical biosensor; and
   determining the concentration of the target bioanalyte in the sample from the change in the light emission.

* * * * *

SEQUENCE LISTING

```
<160> NUMBER OF SEQ ID NOS: 2

<210> SEQ ID NO 1
<211> LENGTH: 8
<212> TYPE: PRT
<213> ORGANISM: Artificial Sequence
<220> FEATURE:
<223> OTHER INFORMATION: MMP Substrate
<220> FEATURE:
<221> NAME/KEY: GABA
<222> LOCATION: (1)..(1)
<223> OTHER INFORMATION: gamma-aminobutyric acid

<400> SEQUENCE: 1

Xaa Pro Gln Gly Leu Gln Ala Lys
1               5

<210> SEQ ID NO 2
<211> LENGTH: 9
<212> TYPE: PRT
<213> ORGANISM: Artificial Sequence
<220> FEATURE:
<223> OTHER INFORMATION: Detection Agent
<220> FEATURE:
<221> NAME/KEY: Dabcyl
<222> LOCATION: (1)..(1)
<223> OTHER INFORMATION: 4-((4-(dimethylamino)phenyl)azo)benzoic acid
<220> FEATURE:
```

-continued

```
<221> NAME/KEY: GABA
<222> LOCATION: (2)..(2)
<223> OTHER INFORMATION: gamma-aminobutyric acid
<220> FEATURE:
<221> NAME/KEY: Q(EDANS)
<222> LOCATION: (7)..(7)
<223> OTHER INFORMATION: Glutamine(5-((2-Aminoethyl)amino)naphthalene-1-
      sulfonic acid)

<400> SEQUENCE: 2

Xaa Xaa Pro Gln Gly Leu Xaa Ala Lys
1               5
```